US010919039B2

(12) United States Patent
Trigub et al.

(10) Patent No.: US 10,919,039 B2
(45) Date of Patent: Feb. 16, 2021

(54) DEVICES WITH MODIFIED CONDUITS

(71) Applicant: Abaxis, Inc., Union City, CA (US)

(72) Inventors: Gregory Trigub, Alameda, CA (US); Robert Justice Shartle, Livermore, CA (US); Warren Edward Farnam, III, Flagstaff, AZ (US); Daniel E. Kuehner, Castro Valley, CA (US)

(73) Assignee: ABAXIS, INC., Union City, CA (US)

( * ) Notice: Subject to any disclaimer, the term of this patent is extended or adjusted under 35 U.S.C. 154(b) by 239 days.

(21) Appl. No.: 16/227,060

(22) Filed: Dec. 20, 2018

(65) Prior Publication Data
US 2019/0168214 A1 Jun. 6, 2019

Related U.S. Application Data

(63) Continuation of application No. PCT/US2017/039460, filed on Jun. 27, 2017.
(Continued)

(51) Int. Cl.
*B01L 3/00* (2006.01)
*G01N 33/48* (2006.01)
(Continued)

(52) U.S. Cl.
CPC ..... *B01L 3/50273* (2013.01); *B01L 3/502707* (2013.01); *B01L 3/502746* (2013.01);
(Continued)

(58) Field of Classification Search
CPC ........... B01L 3/50273; B01L 3/502707; B01L 3/502746; B01L 3/00; B29C 65/08; G01N 33/48; G01N 35/00
See application file for complete search history.

(56) References Cited

U.S. PATENT DOCUMENTS

| 4,990,075 A | 2/1991 | Wogoman |
| 5,061,381 A | 10/1991 | Burd |
(Continued)

FOREIGN PATENT DOCUMENTS

| EP | 1192006 A1 | 4/2002 |
| WO | WO 2000/078455 A1 | 12/2000 |
(Continued)

OTHER PUBLICATIONS

Extended European Search Report for EP Application No. 17821066.2, dated Nov. 15, 2019, 8 pages.
(Continued)

*Primary Examiner* — Brian J. Sines
(74) *Attorney, Agent, or Firm* — Cooley LLP

(57) ABSTRACT

A centrifugal rotor device includes a first chamber configured to hold a fluid, and a second chamber configured to receive the fluid from the first chamber. The centrifugal rotor device also includes a conduit coupled to the first chamber at a conduit inlet and coupled to the second chamber at a conduit outlet, the conduit configured to permit movement of the fluid from the first chamber to the second chamber. The conduit includes a first channel and a second channel formed adjacent to the first channel. The second channel is in fluid communication with the first channel and has a dimension smaller than the smallest dimension of the first channel. The conduit also includes one or more obstructive features present in the second channel configured to impede movement of the fluid in the second channel.

20 Claims, 27 Drawing Sheets

Related U.S. Application Data

(60) Provisional application No. 62/355,168, filed on Jun. 27, 2016.

(51) Int. Cl.

| | | |
|---|---|---|
| *G01N 35/00* | (2006.01) | |
| *B29C 65/08* | (2006.01) | |
| *G01N 33/49* | (2006.01) | |
| *B29C 65/00* | (2006.01) | |
| *B29C 65/82* | (2006.01) | |
| *G01N 21/07* | (2006.01) | |
| *B29L 31/00* | (2006.01) | |

(52) U.S. Cl.
CPC .......... *B29C 65/08* (2013.01); *B29C 65/8253* (2013.01); *B29C 66/1122* (2013.01); *B29C 66/244* (2013.01); *B29C 66/30221* (2013.01); *B29C 66/30223* (2013.01); *B29C 66/54* (2013.01); *G01N 33/48* (2013.01); *G01N 33/491* (2013.01); *B01L 2200/0605* (2013.01); *B01L 2200/0621* (2013.01); *B01L 2200/12* (2013.01); *B01L 2300/0806* (2013.01); *B01L 2300/0864* (2013.01); *B01L 2300/0867* (2013.01); *B01L 2400/0406* (2013.01); *B01L 2400/0409* (2013.01); *B01L 2400/086* (2013.01); *B01L 2400/088* (2013.01); *B29L 2031/7498* (2013.01); *G01N 21/07* (2013.01)

(56) References Cited

U.S. PATENT DOCUMENTS

| | | |
|---|---|---|
| 5,122,284 A | 6/1992 | Braynin et al. |
| 5,173,193 A | 12/1992 | Schembri |
| 5,186,844 A | 2/1993 | Burd et al. |
| 5,242,606 A | 9/1993 | Braynin et al. |
| 5,275,016 A | 1/1994 | Chatterjee et al. |
| 5,304,348 A | 1/1994 | Chatterjee et al. |
| 5,413,732 A | 5/1995 | Buhl et al. |
| 5,472,603 A | 12/1995 | Schembri |
| 5,518,930 A | 5/1996 | Burd |
| 5,591,643 A | 1/1997 | Schembri |
| 6,063,589 A * | 5/2000 | Kellogg .............. B01F 13/0059 366/DIG. 3 |
| 6,632,399 B1 * | 10/2003 | Kellogg .............. B01F 13/0059 422/505 |
| 7,998,411 B2 | 8/2011 | Kopf-Sill et al. |
| 2002/0119536 A1 | 8/2002 | Stern |
| 2003/0207457 A1 | 11/2003 | Kopf-sill et al. |
| 2004/0202579 A1 | 10/2004 | Larsson et al. |
| 2005/0041525 A1 | 2/2005 | Pugia et al. |
| 2005/0109396 A1 * | 5/2005 | Zucchelli .............. F16K 99/003 137/67 |
| 2005/0239210 A1 | 10/2005 | Iida et al. |
| 2006/0254916 A1 | 11/2006 | Hernandez et al. |
| 2007/0026416 A1 | 2/2007 | Fuchs |
| 2007/0072290 A1 | 3/2007 | Hvichia et al. |
| 2007/0095393 A1 * | 5/2007 | Zucchelli .............. F16K 99/0001 137/68.11 |
| 2010/0266450 A1 | 10/2010 | Wimberger-Friedl et al. |
| 2010/0301022 A1 | 12/2010 | Rickwood et al. |
| 2011/0094600 A1 * | 4/2011 | Bergeron .......... B01L 3/502738 137/38 |
| 2011/0243813 A1 | 10/2011 | Jackinsky et al. |
| 2012/0314528 A1 * | 12/2012 | Roth .................... B01F 13/0059 366/160.5 |
| 2013/0344496 A1 * | 12/2013 | Peytavi .............. B01L 3/502715 435/6.12 |
| 2014/0045186 A1 | 2/2014 | Gubatayao et al. |
| 2016/0256869 A1 | 9/2016 | Ayliffe |

FOREIGN PATENT DOCUMENTS

| | | |
|---|---|---|
| WO | WO 2018/005464 A1 | 1/2018 |
| WO | WO 2018/195530 A1 | 10/2018 |

OTHER PUBLICATIONS

PCT/US2017/039460, International Preliminary Report on Patentability, dated Nov. 13, 2017, 6 pages.
PCT/US2017/039460, International Search Report and Written Opinion, dated Nov. 13, 2017, 9 pages.
PCT/US2018/028855, International Preliminary Report on Patentability, dated Oct. 22, 2019, 10 pages.
PCT/US2018/028855, International Search Report and Written Opinion, dated Jul. 6, 2018, 12 pages.

* cited by examiner

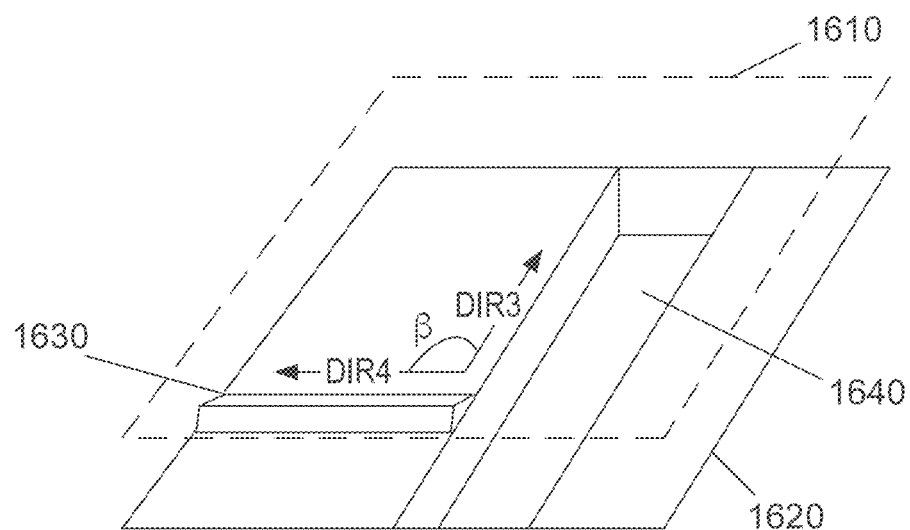
FIG. 16A
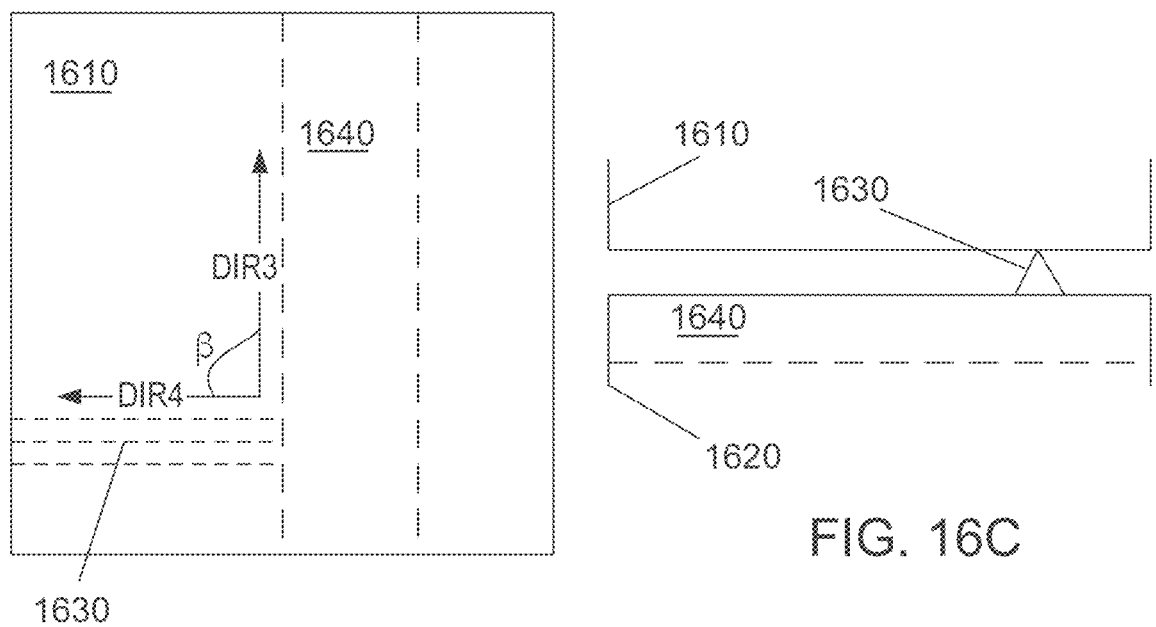
FIG. 16C
FIG. 16B

1700

1710

Placing a first side of a first substrate in contact with a first side of a second substrate to form a channel therebetween, the second substrate including an energy director formed on the first side of the second substrate, the channel including a first channel and a second channel adjacent to the first channel, the second channel in fluid communication with the first channel, the second channel having a dimension smaller than a smallest dimension of the main channel, the energy director being relatively proximate to the second channel and relatively distal to the first channel

1720

Bonding the first substrate and the second substrate by applying high frequency sounds to the energy director to form a weld, at least a portion of the weld extending into the second channel in the form of an obstructive feature, the obstructive feature configured to impede movement of fluid in the second channel during use

FIG. 17

DEVICES WITH MODIFIED CONDUITS

CROSS-REFERENCE TO RELATED APPLICATIONS

This application is a continuation of International Patent Application No. PCT/US2017/039460, filed on Jun. 27, 2017, which claims priority to U.S. Provisional Patent Application Ser. No. 62/355,168, filed on Jun. 27, 2016, the content of each of which is hereby incorporated by reference in its entirety.

BACKGROUND

In some centrifugal rotor devices, capillary-flow fronts can form along the edges of main siphon channels, such as in small regions not filled by energy-director melt flow during ultrasonic cover welding. If such flow fronts reach the channel outlet while the rotor is still spinning, they can, among other problems, rupture under centrifugal pressure.

There is hence an unmet need for improved conduit design in centrifugal rotor devices.

SUMMARY

Some embodiments are directed to a centrifugal rotor device that includes a first chamber configured to hold a fluid, and a second chamber configured to receive the fluid from the first chamber. The centrifugal rotor device also includes a conduit coupled to the first chamber at a conduit inlet and coupled to the second chamber at a conduit outlet, the conduit configured to permit movement of the fluid from the first chamber to the second chamber. The conduit includes a first channel and a second channel formed adjacent to the first channel. The second channel is in fluid communication with the first channel and has a dimension smaller than the smallest dimension of the first channel. The conduit also includes one or more obstructive features present in the second channel configured to impede movement of the fluid in the second channel.

Some embodiments are directed to a centrifugal rotor device that includes a rim defining a radially inward direction and a radially outward direction, and a first chamber configured to receive a set of fluids. The first chamber is further configured to substantially mix the set of fluids to generate a mixed fluid during use, and includes a side wall. The centrifugal rotor device also includes a conduit including a coupling portion coupled to the side wall of the first chamber at a conduit inlet, the conduit being in fluid communication with the first chamber. The coupling portion is formed between the radially inward direction and a direction perpendicular to the radially inward direction at an angle of from about 0 degrees to about 180 degrees from the radially inward direction, and disposed at a distance of from about 0.025 mm to about 1 mm from a radially outward edge of the side wall.

Some embodiments are directed to a centrifugal rotor device that includes a rim defining a radially inward direction and a radially outward direction. The centrifugal rotor device also includes a first chamber configured to receive a set of fluids. The first chamber is further configured to substantially mix the set of fluids to generate a mixed fluid during use, the first chamber including a side wall. The centrifugal rotor device also includes a conduit including a coupling portion coupled to the side wall of the first chamber at a conduit outlet, the conduit being in fluid communication with the first chamber. The coupling portion is formed between the radially inward direction and a direction perpendicular to the radially inward direction at an angle of from about 0 degrees to about 180 degrees from the radially inward direction.

Some embodiments are directed to a centrifugal rotor device that includes an outer rim defining a radially inward direction and a radially outward direction, and a first chamber configured to receive a set of fluids. The first chamber is further configured to substantially mix the set of fluids to generate a mixed fluid during use, and includes a side wall. The centrifugal rotor device also includes a conduit including a coupling portion coupled to the side wall of the first chamber at a conduit inlet, the conduit being in fluid communication with the first chamber, the coupling portion disposed at a distance of from about 0.025 mm to about 1 mm from a radially outward edge of the side wall.

Some embodiments are directed to a centrifugal rotor device that includes a rim defining a radially inward direction and radially outward direction, and a first chamber configured to receive a set of fluids. The first chamber is further configured to substantially mix the set of fluids to generate a mixed fluid during use, the first chamber including an interior portion and a side wall. The centrifugal rotor device also includes a conduit coupled to the side wall of the first chamber at a conduit inlet, the conduit being in fluid communication with the first chamber. The conduit inlet is formed between the radially inward direction and a direction perpendicular to the radially inward direction at an angle greater than zero degrees from the radially inward direction.

Some embodiments are directed to a method of fabricating a device that includes placing a first side of a first substrate in contact with a first side of a second substrate to form a channel therebetween, the first substrate including an energy director formed on the first side of the first substrate. The method also includes bonding the first substrate and the second substrate by applying high frequency sounds to the energy director to form a weld around the channel, at least a portion of the weld extending into the channel. An edge of the energy director is formed at an angle of from about 20 degrees to about 160 degrees with respect to a longitudinal direction of the channel.

Some embodiments are directed to a method of fabricating a device that includes placing a first side of a first substrate in contact with a first side of a second substrate to form a channel therebetween, the first substrate including an energy director formed on the first side of the first substrate. The channel includes a first channel and a second channel adjacent to the first channel, the second channel in fluid communication with the first channel. The second channel has a dimension smaller than a smallest dimension of the main channel, the energy director being relatively proximate to the second channel and relatively distal to the first channel. The method also includes bonding the first substrate and the second substrate by applying high frequency sounds to the energy director to form a weld. At least a portion of the weld extending into the second channel in the form of an obstructive feature configured to impede movement of fluid in the second channel during use.

BRIEF DESCRIPTION OF THE DRAWINGS

FIGS. 16A-16C are example illustrations of a weld joint adjacent to a channel, according to embodiments. FIG. 16A is a perspective view of an arrangement including portions of a first substrate including a weld joint and a second substrate having a channel formed thereon. FIG. 16B is a top view of the arrangement of FIG. 16A. FIG. 16C is a side view of the arrangement of FIG. 16A.

FIG. 17 is another method of fabricating a device, according to embodiments.

DETAILED DESCRIPTION

Figure 1A:
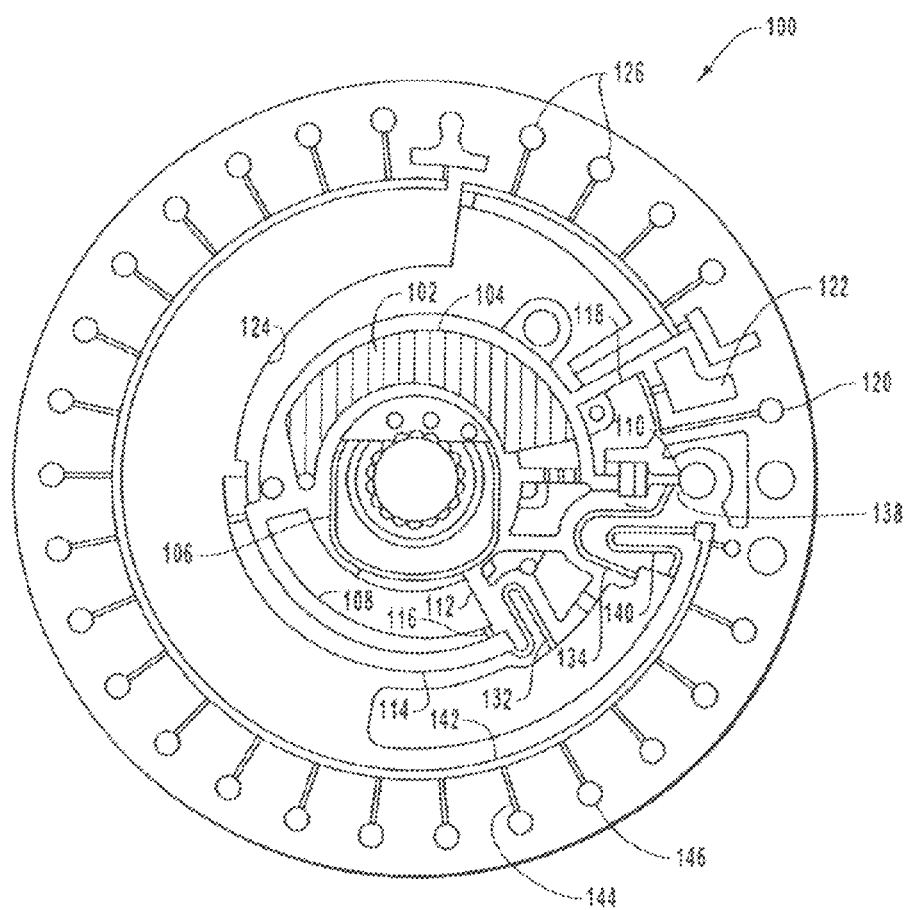
FIGS. 1A-1G are illustrations of a centrifugal rotor device, according to embodiments.

The present invention provides methods and devices for the delivery of liquids to chambers in a centrifugal rotor device. The rotors can include conduits which ensure precise delivery of metered volumes of liquid to a desired chamber in the rotor.

The centrifugal rotor devices as disclosed herein are suitable for the analysis of any liquid, typically a biological sample such as whole blood or plasma. It can also be useful with numerous other biological fluids, such as urine, sputum, semen, saliva, ocular lens fluid, cerebral fluid, spinal fluid, amniotic fluid. Other fluids that can be tested include tissue culture media, food and industrial chemicals.

The rotors include chambers which can separate cellular components from the biological sample (e.g. whole blood), measure a precise volume of liquid sample (e.g. plasma), mix the sample with an appropriate diluent and deliver the diluted sample to cuvettes for optical analysis. The fluid delivered to the cuvettes, undergoes reaction(s) within the cuvettes, e.g., reaction with a reagent which forms part of an analytical procedure to detect one or more analytes within the fluid. The sample may further be optically analyzed while present in the rotor, either with or without prior reaction.

Analytical rotor devices as disclosed herein can include a rotor body which is capable of being mounted on a conventional laboratory centrifuge of the type which is commercially available from suppliers, such as Beckman Instruments, Inc., Spinco Division, Fullerton, Calif.; Fisher scientific, Pittsburgh, Pa.; VWR Scientific, San Francisco, Calif., and/or the like. The centrifugal rotor device can include a receptacle and/or other coupling device suitable for mounting on a vertical drive shaft provided by the centrifuge. The particular design of the receptacle or coupling device can depend on the nature of the centrifuge, and it will be appreciated that the centrifugal rotor devices disclosed herein may be adapted for use with all or most types of centrifuges which are now available or which may become available in the future. Aspects of the rotor devices as disclosed herein can include one or more of: reagent container as disclosed in U.S. Pat. No. 5,304,348; sample metering as disclosed in U.S. Pat. No. 5,242,606; mixing chamber as disclosed in U.S. Pat. No. 5,472,603; cuvettes/chambers for optical analysis of biological fluids as disclosed in U.S. Pat. No. 5,122,284; and one or more inlet channels as disclosed in U.S. Pat. No. 5,591,643.

The rotor body can include a structure which maintains a desired geometric pattern or relationship between a plurality of chambers, interconnection passages, and vents, as described in more detail below. Various specialized chambers and channels suitable for use in the rotors of the invention are disclosed in U.S. Pat. Nos. 5,061,381; 5,122,284; and 7,998,411, and U.S. Ser. Nos. 07/678,762 and 07/783,041, the entire disclosures of each of which are incorporated herein by reference.

In some embodiments, the rotor body can be a substantially solid plate or disk with the chambers and passages formed as spaces or voids in the otherwise solid matrix. Such solid plate structures may be formed by, for example, laminating a plurality of separately-formed layers together into a composite structure where the chambers and horizontal passages are generally formed between adjacent layers. The vertical passages may be formed through the layers. The individual layers may be formed by injection molding, machining, or combinations thereof, and will usually be joined together, typically using a suitable adhesive or by ultrasonic welding. The final enclosed volumes are formed when the layers are brought together.

In some embodiments, the centrifugal rotor device could be formed as a plurality of discrete components, such as tubes, vessels, chambers, etc., arranged in a suitable framework.

The rotor body may be formed from a wide variety of materials, and in some embodiments, may include two or more materials. In some embodiments, the material(s) can be transparent so that the presence and distribution of the biological fluid, cellular components, and reagents may be observed within the various internal chambers and passages. In some embodiments, to the extent analytical chambers, e.g., cuvettes, or other test wells are formed within the rotor, suitable optical paths can be formed within the rotor so that the contents of the cuvettes may be observed spectrophotometrically, fluorometrically, or by other optical assessment instruments. The construction of suitable cuvettes having particular optical paths formed therethrough is disclosed in U.S. Pat. No. 5,173,193, the entire disclosure of which is incorporated herein by reference. In some embodiments, the centrifugal rotor device can be formed with an acrylic resin having suitable optical properties, at least in those areas which define an optical path.

The devices and methods disclosed herein can be suitable for performing a wide variety of analytic procedures and assays which are beneficially or necessarily performed on blood plasma and other samples. The analytic procedures may require that the sample be combined with one or more reagents so that some detectable change occurs which may be related to the presence and/or amount of a particular component (analyte) or characteristic of the sample. For instance, the sample may undergo a reaction or other change which results in a change in color, fluorescence, luminescence, or the like, which may be measured by conventional spectrophotometers, fluorometers, light detectors, and the like. In some cases, immunoassays and other specific binding assays may be performed within the cell-free fluid collection chamber or within cuvettes which are connected to the collection chamber. In some cases, such assay procedures can be homogeneous and not require a separation step. In other cases, heterogeneous assay systems can be included by providing a means to separate the sample (e.g., blood plasma) from the collection chamber or another test well or cuvette after the immunological reaction step has occurred. Any of a number of analytical methods can be adapted for use in the centrifugal rotor devices disclosed herein, depending upon the particular sample being analyzed and component being detected.

In the case of blood analyses, conventional blood assays are typically performed. Examples of assays which may be performed include those designed to detect glucose, lactate, dehydrogenase, serum glutamic-oxaloacetic transaminase (SGOT), serum glutamic-pyruvic transaminase (SGPT), blood urea nitrogen (BUN), total protein, alkalinity, phosphatase, bilirubin, calcium, chloride, sodium, potassium, magnesium, and the like. This list is not exhaustive and is intended merely as being exemplary of the assays which may be performed using the devices and methods disclosed herein. In some embodiments, these tests will require that the blood and plasma be combined with one or more reagents which result in an optically detectable, usually photometrically detectable, change in the plasma. The reagents which are required are well known and amply described in the patent and scientific literature.

The reagents can be provided in lyophilized form to increase stability. In some embodiments, the reagents are provided in the form of lyophilized reagent spheres as described in U.S. Pat. No. 5,413,732, the entire disclosure of which is incorporated herein by reference.

Referring now to FIGS. 1A-F, an analytical centrifugal rotor device 100 (also sometimes referred to as a rotor) including chambers and channels is illustrated. Described here during use for purposes of explanation, FIG. 1A shows the position of a (as an example, non-limiting sample fluid) blood sample 102 in the blood application chamber 104 after the sample has been loaded in the rotor body 100. A diluent container in chamber 106 is opened upon mounting of the rotor on the spindle of the centrifuge as described in commonly assigned U.S. Pat. No. 5,275,016, the entire disclosure of which is incorporated herein by reference. Generally, the fluids described herein (i.e., the sample and/or diluent) are illustrated in FIGS. 1A-1F by hatched lines.

Figure 1B:
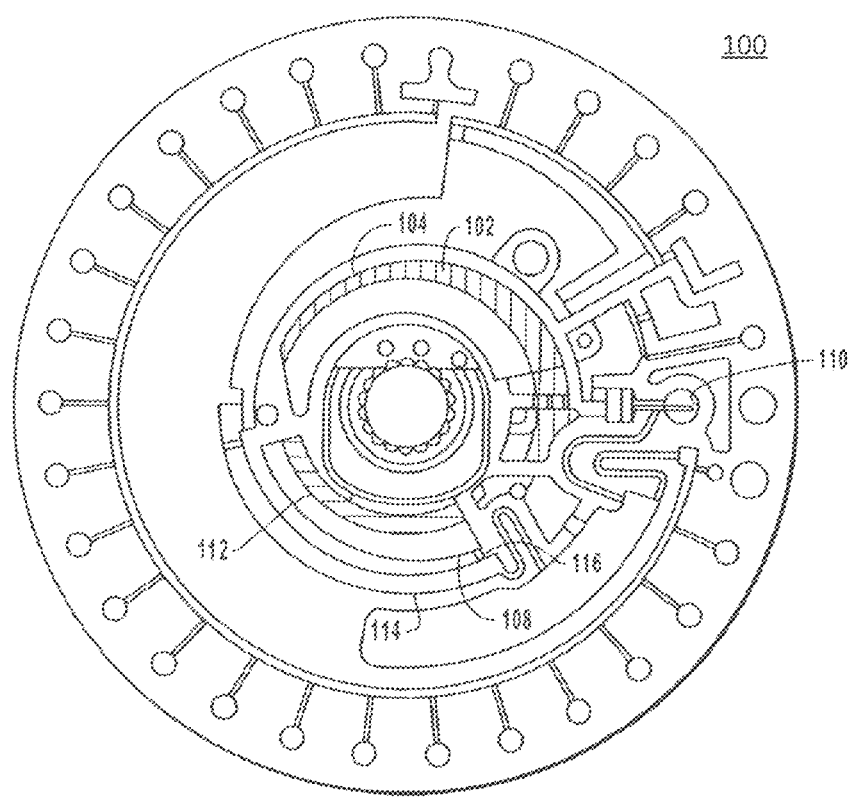
Figure 1C:
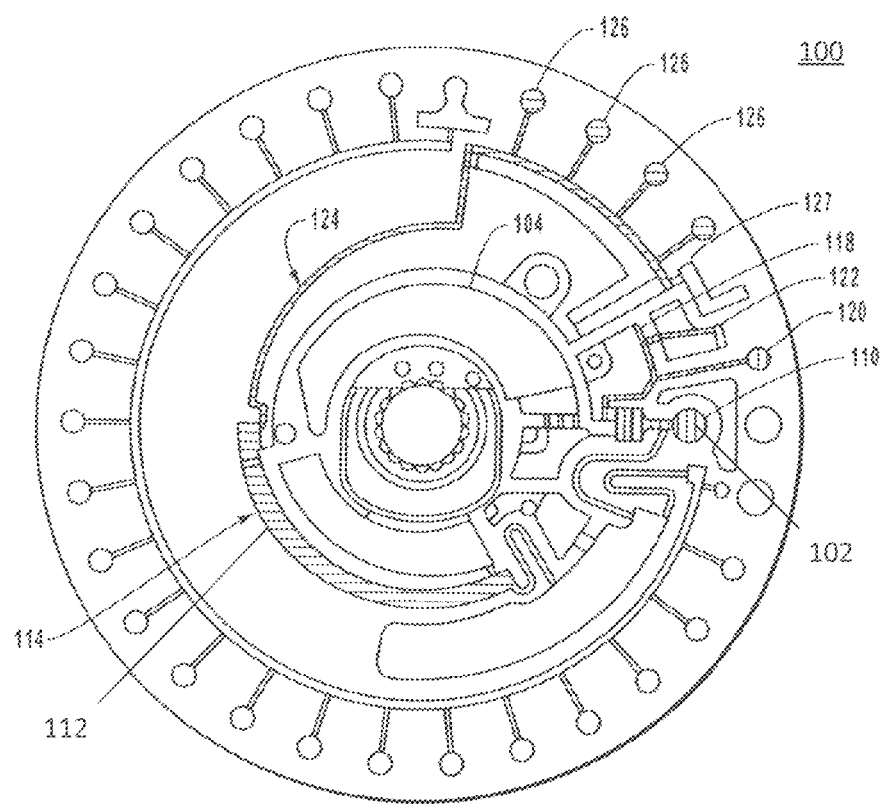

FIG. 1B shows the position of the diluent 108 and blood sample 102 after the rotor is spun at a suitable revolutions per minute (rpm) such as, for example, at 1,000 rpm, at 2,000 rpm, at 3,000 rpm, at 4,000 rpm, at 5,000 rpm, at 6,000 rpm, including all values and sub ranges in between. The blood sample 102 begins to exit the blood application chamber 104 and enters the plasma metering chamber 110. At the same time, diluent 112 empties from the diluent container into the holding chamber 108. The diluent substantially immediately begins to enter the diluent metering chamber 114 through channel 116.

Still referring to FIGS. 1A-1F, FIG. 1C shows the position of the liquids as the rotor 100 continues to spin. Here, the blood sample 102 has emptied the blood application chamber 104 and overflows the plasma metering chamber 110 into the overflow chamber 118 where it flows to the hemoglobin cuvette 120 and the excess blood dump 122. Meanwhile, diluent 112 fills the diluent metering chamber 114 and excess flows through channel 124 to diluent-only cuvettes 126 and excess diluent dump 127.

Figure 1D:
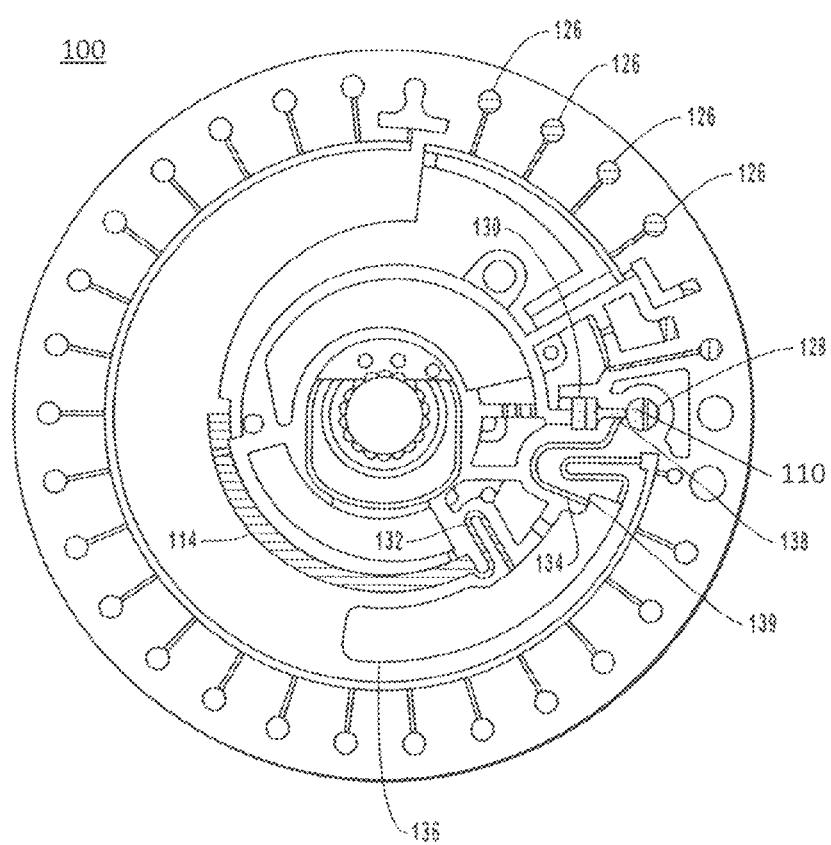

FIG. 1D shows the position of the liquids at the conclusion of the first spin. The blood sample 102 has separated into cells 128 and plasma 130. The diluent-only cuvettes 126 are filled and a predetermined amount of diluent remains in the diluent metering chamber 114. The rotor 100 is then stopped and conduit 132 (also sometimes referred to as a siphon) from the diluent metering chamber 114, as well as the conduit 134 from the plasma metering chamber 110, are allowed to prime, as described above. Conduit 134 is a conduit of the present invention. It is connected to the plasma metering chamber 110 at inlet 138. The inlet 138 is positioned radially outward of the conduit outlet 139, through which the conduit 134 empties into the mixing chamber 136.

Figure 1E:
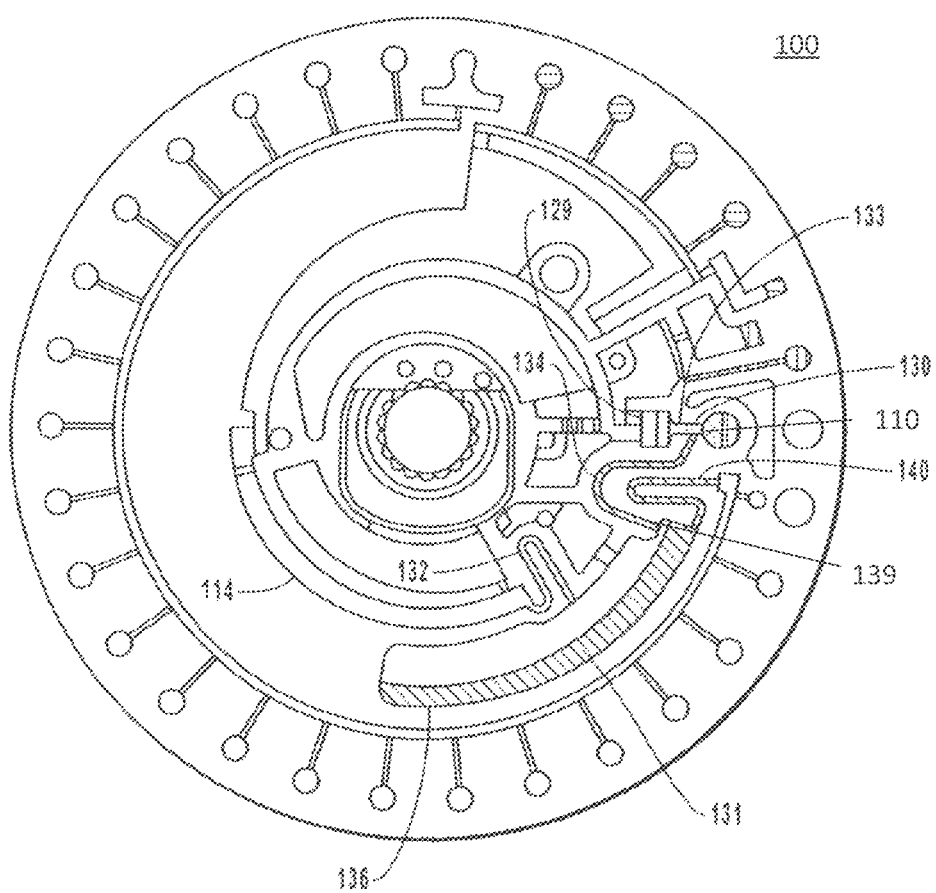

FIG. 1E shows the position of the liquids during the second spin of the rotor 100. The diluent metering chamber 114 empties into the mixing chamber 136 through conduit 132. A predetermined amount of plasma 130 is metered into the mixing chamber 136 and the two fluids are mixed, thereby forming diluted plasma 131. The amount of plasma 130 delivered to the mixing chamber 136 is determined by the position of the outlet 139 on the conduit 134. As can be seen in this figure, the final level of the plasma 133 in the plasma metering chamber 110 is at the same radial position as the outlet 139. Thus, the volume of plasma delivered to the mixing chamber 136 is determined by the volume of the plasma metering chamber 110 between the exit to the overflow chamber 129 and the final level of plasma 133. After the plasma and diluent are mixed in the mixing chamber 136, the rotor is stopped again and the output conduit 140 is primed.

Figure 1F:
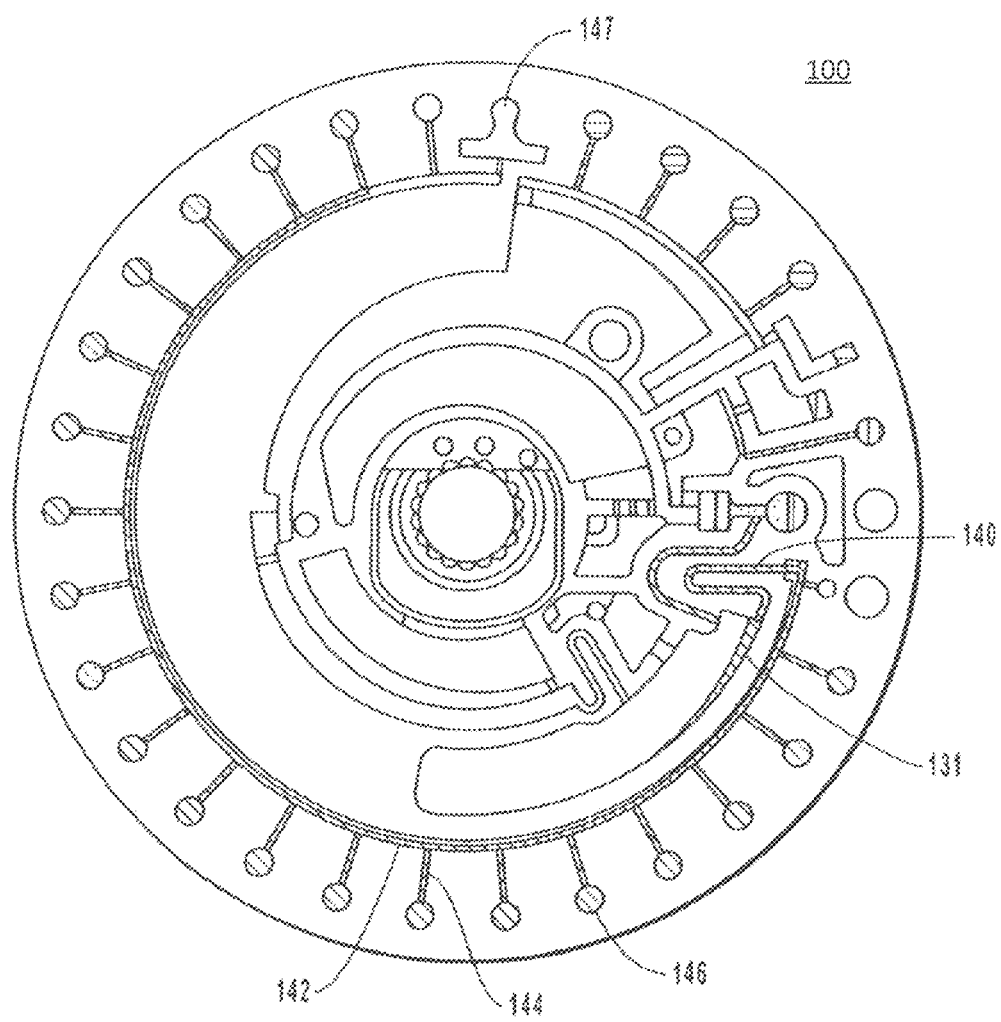

FIG. 1F shows the position of the diluted plasma 131 as the rotor is spun during the third spin. This figure illustrates the movement of the diluted plasma 131 through the distribution ring 142 and inlet channels 144 to the cuvettes 146 and excess diluted plasma dump 147. The resistance to flow in the output conduit 140 is selected to be higher than the resistance to flow in the distribution ring 142 and the inlet channels 144 so that air present in the cuvettes 146 can escape as the cuvettes are filled. Specifically, conduit 140 is dimensioned such that the ratio of the cross sectional area of the inlet channels 144 to the cross sectional area of the liquid in them is greater than 2:1, preferably greater than about 4:1. The cross sectional area of the inlet channels 144 is typically the same as or slightly smaller than that of the distribution channel 142 so that gas in the unvented cuvettes escapes through the inlet channels 144 and distribution 142. If the sample is plasma, or diluted plasma and the channels are rectangular in cross-section, their dimensions are typically as follows: conduit: 0.150 mm depth, 0.200 mm width, 0.100 mm depth, 0.200 mm width; distribution channel 0.300 mm depth, 0.5 mm width; inlet channels: 0.150 depth, 0.500 width, including all values and subranges in between.

After the cuvettes have been filled, reagents present in the cuvettes are mixed with the solution and the necessary photometric analyses are made on the sample. Such analyses are carried out as described above according to methods known to those of skill in the art. Although the foregoing invention has been described in detail for purposes of clarity of understanding, it will be obvious that certain modifications may be practiced within the scope of the appended claims.

Figure 1G:
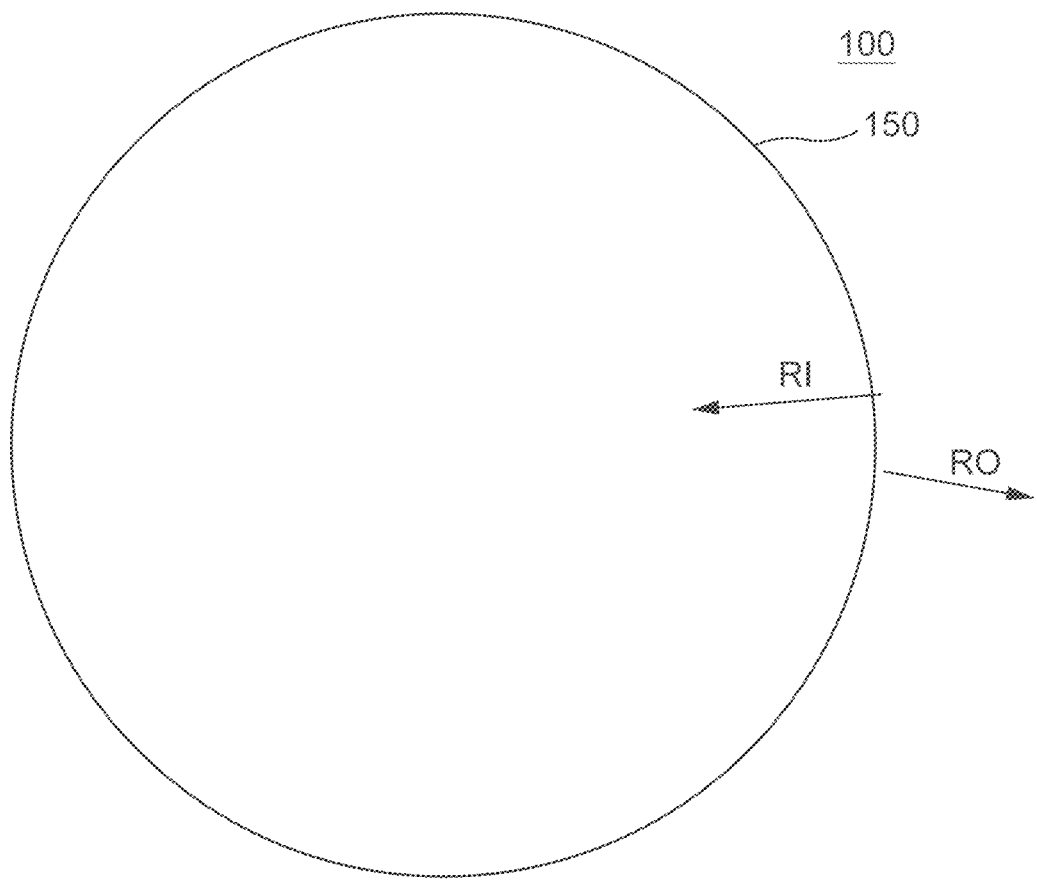

FIG. 1G illustrates a rim 150 of the rotor 100. The rim 150 defines a radially inward direction RI and a radially outward direction RO for the rotor 100.

Some embodiments disclosed herein, and described in greater detail below are directed to a centrifugal rotor device including a first chamber configured to hold a fluid, and a second chamber configured to receive the fluid from the first chamber. The centrifugal rotor device can further include a conduit coupled to the first chamber at a conduit inlet and coupled to the second chamber at a conduit outlet, the conduit configured to permit movement of the fluid from the first chamber to the second chamber. The conduit includes a first channel and a second channel formed adjacent to the first channel. The second channel is in fluid communication with the first channel and has a dimension smaller than the smallest dimension of the first channel. The conduit also includes one or more obstructive features present in the second channel configured to impede movement of the fluid in the second channel.

Figure 2:
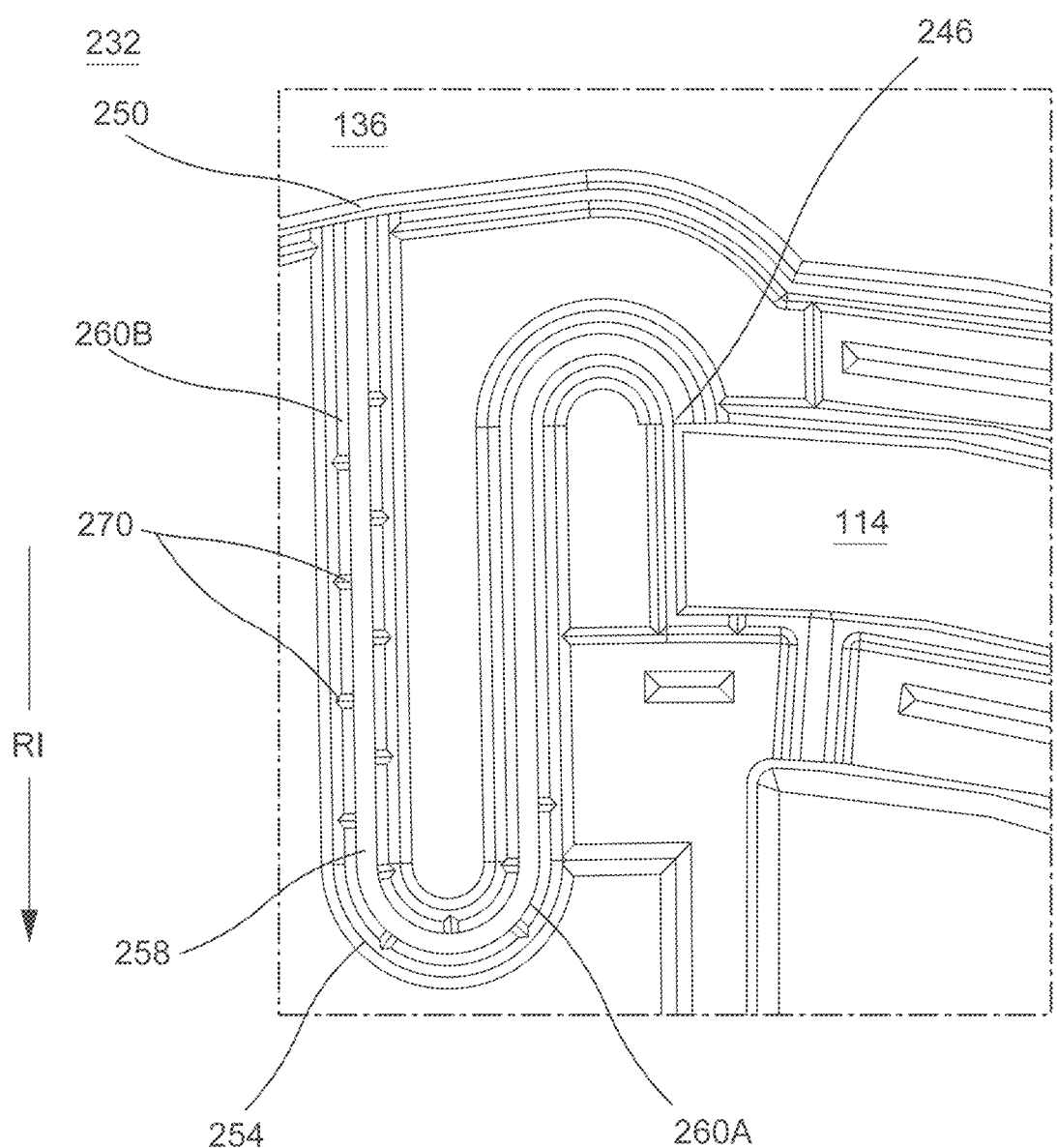
FIG. 2 is an illustration of a conduit of a centrifugal rotor device, according to embodiments.

FIG. 2 illustrates a magnified view of the conduit 132 (illustrated herein as reference character 232), according to embodiments. The conduit 232 includes an inlet portion 246 coupled to the chamber 114 (also sometimes referred to as a first chamber) and an outlet portion 250 coupled to the chamber 136 (also sometimes referred to as a second chamber). The conduit 232 also includes a curved portion 254 that is radially inward (see FIGS. 1A-1G, 2) from the radially outermost of the inlet portion 246 and the outlet portion 250. In this manner, fluid flow in the conduit 232 at undesirable times (e.g., at certain rpm values and/or rpm ranges) during use can be prevented by maintaining the curved portion at a relatively inward position.

The term "inlet portion" as used herein with reference to a conduit refers to a section of the conduit from the conduit inlet to about 1 mm along the length of the conduit. The term "outlet portion" as used herein with reference to a conduit refers to a section of the conduit from the conduit outlet to about 0.05 mm along the length of the conduit. The term "curved portion" as used herein with reference to a conduit refers to a section of the conduit between the inlet portion and the outlet portion, and being non-linear at least in part.

The conduit 232 also includes a main/first channel 258 and second/auxiliary channels 260A, 260B (sometimes referred to as a first auxiliary channel and a second auxiliary channel, respectively) formed on either side of the first channel. In some embodiments, the second channels 260A, 260B are a byproduct of a manufacturing process such as, for example, ultrasonic welding. For example, it is possible that during ultrasonic welding, the weld resulting in the formation of the first channel 258 leaves regions adjacent to the first channel, resulting in the formation of one or more of the second channels 260A, 260B. In other embodiments, the second channels 260A, 260B are formed by deliberate design.

The inner space/volume of the second channels 260A, 260B can be continuous with an inner space/volume of the first channel 258. Referring to the second channel 260A for purposes of explanation, in some embodiments, at least one dimension of the second channel 260A is smaller than the smallest dimension of the first channel 258. For example, if the smallest dimension of the first channel is a depth of the first channel 258, than a width or depth of the second channel 260A can be smaller than the depth of the first channel 258, and so on. In this manner, fluid flow in the second channels 260A, 260B can exhibit different characteristics than the first channel 258, and can be accounted for. For example, in some embodiments, the dimensions of the second channels 260A, 260B can result in increased capillary action, leading to a differential/higher flow rate in the second channel than in the first channel 258.

In some embodiments, and as illustrated in FIG. 2, one or more obstructive features 270 can be disposed, created, adhered, and/or otherwise formed in one or more of the second channels 260A, 260B. In some embodiments, the obstructive features 270 can be any suitable component configured for impeding fluid flow in the second channels 260A, 260B. As a non-limiting example, in some embodiments, the obstructive features 270 can be fluidphobic (e.g., hydrophobic, or otherwise configured to repel the fluid in the channel) regions in the second channels 260A, 260B that are formed during or after manufacture. As another example, the obstructive features 270 can be a stop that is formed during manufacture, such as a welded region/stop formed in the second channels 260A, 260B during ultrasonic welding.

The obstructive features 270 can be formed substantially along the entire length of the conduit 232, or any portion thereof. For example, and as illustrated in FIG. 2, the obstructive features can be formed in a linear and/or curved portions of 260A, 260B. In some embodiments (and as illustrated in FIG. 2) where the obstructive features 270 are formed in both second channels 260A, 260B, the obstructive features can be formed in each second channel independent of the other. For example, in some embodiments, at least one obstructive feature is formed in the second channel 260A directly across from an obstructive feature in the channel 260B, i.e., at the same point along the length of the conduit 232. In some embodiments, at least one obstructive feature is formed in the second channel 260A at a different point along the length of the conduit 232 than an obstructive feature in the channel 260B. In some embodiments, each obstructive feature is formed at a different point along the length of the channel 232, i.e., the obstructive features in the channel 260A are staggered from the obstructive features in the channel 260B.

In some embodiments, the spacing between any two of the obstructive features 270, whether formed along the channel 260A or on different channels 260A, 260B, can be about 0.2 mm, about 0.5 mm, about 1 mm, about 1.5 mm, about 2 mm, about 2.5 mm, about 3 mm, about 4 mm, including all values and subranges in between. In some embodiments, the obstructive features 270 can be disposed wholly within the second channels 260A, 260B, while in other embodiments, at least a portion of the obstructive features 270 can protrude into the first channel 258. In some embodiments, the obstructive features 270 can occlude at least 10%, at least 20%, at least 30%, at least 40%, at least 50%, at least 60%, at least 70%, at least 80%, at least 90%, at least 90%, at least 99%, about 100%, of the cross-section of the second channel where formed, including all values and subranges in between.

Figure 3B:
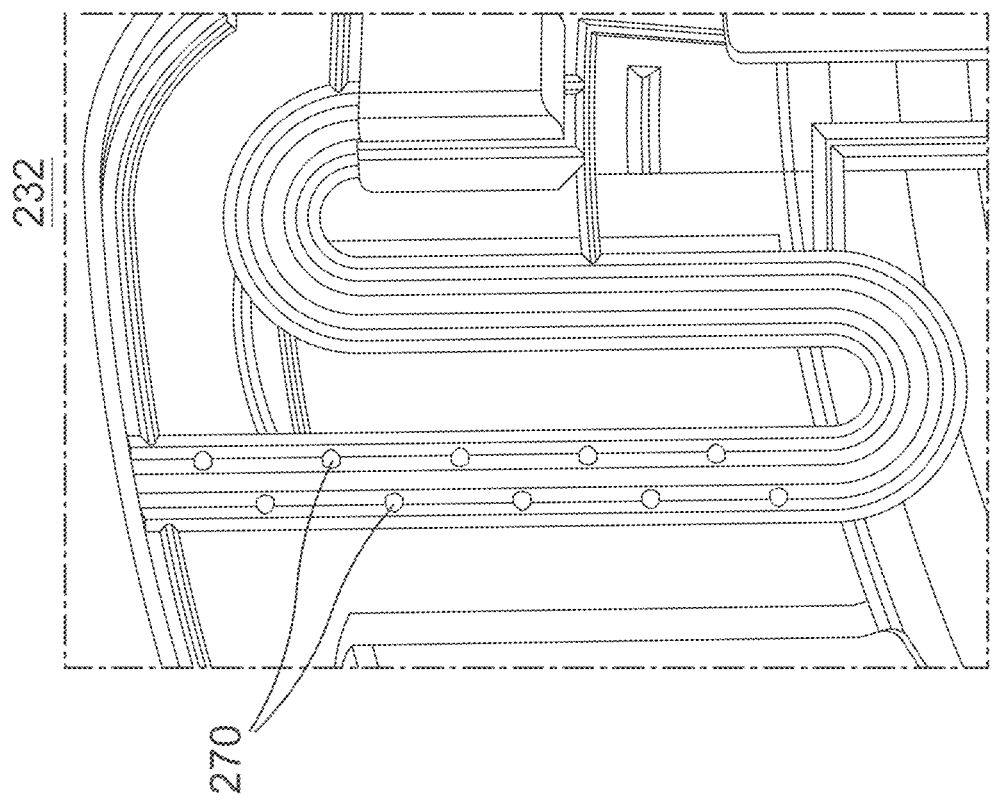
FIGS. 3A-3D illustrate variations in design of the conduit of FIG. 2, according to embodiments.
Figure 3A:
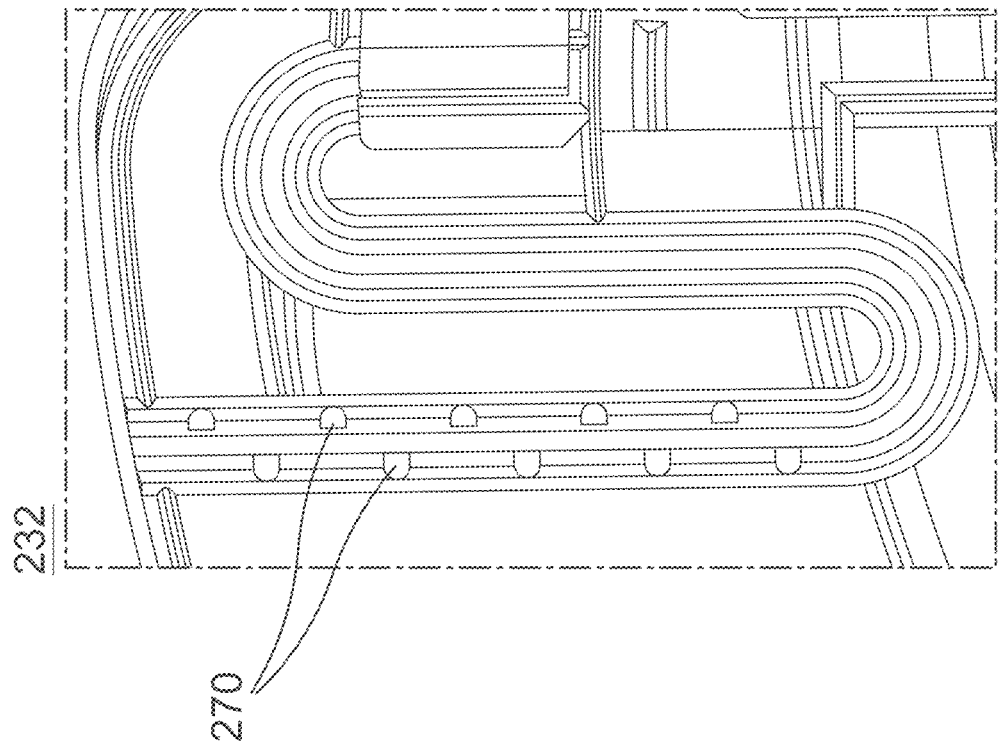
Figure 3D:
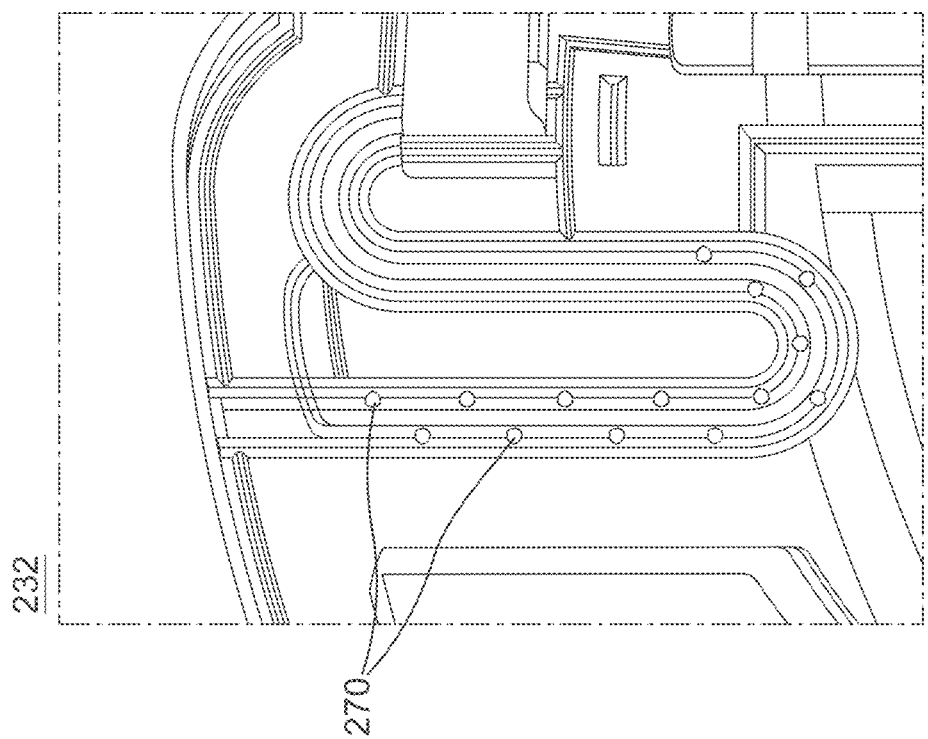
Figure 3C:
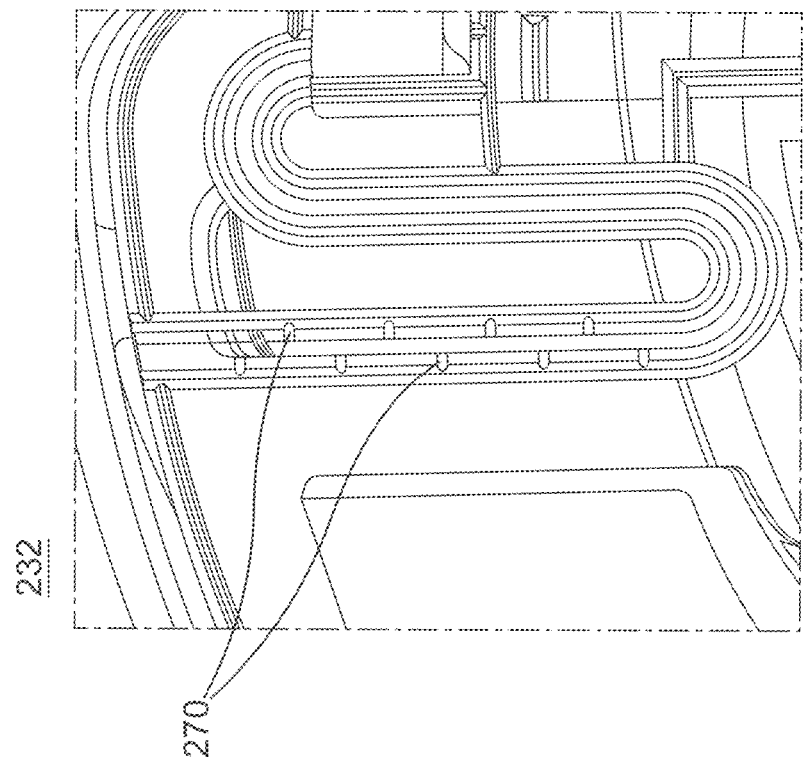
Figure 4:
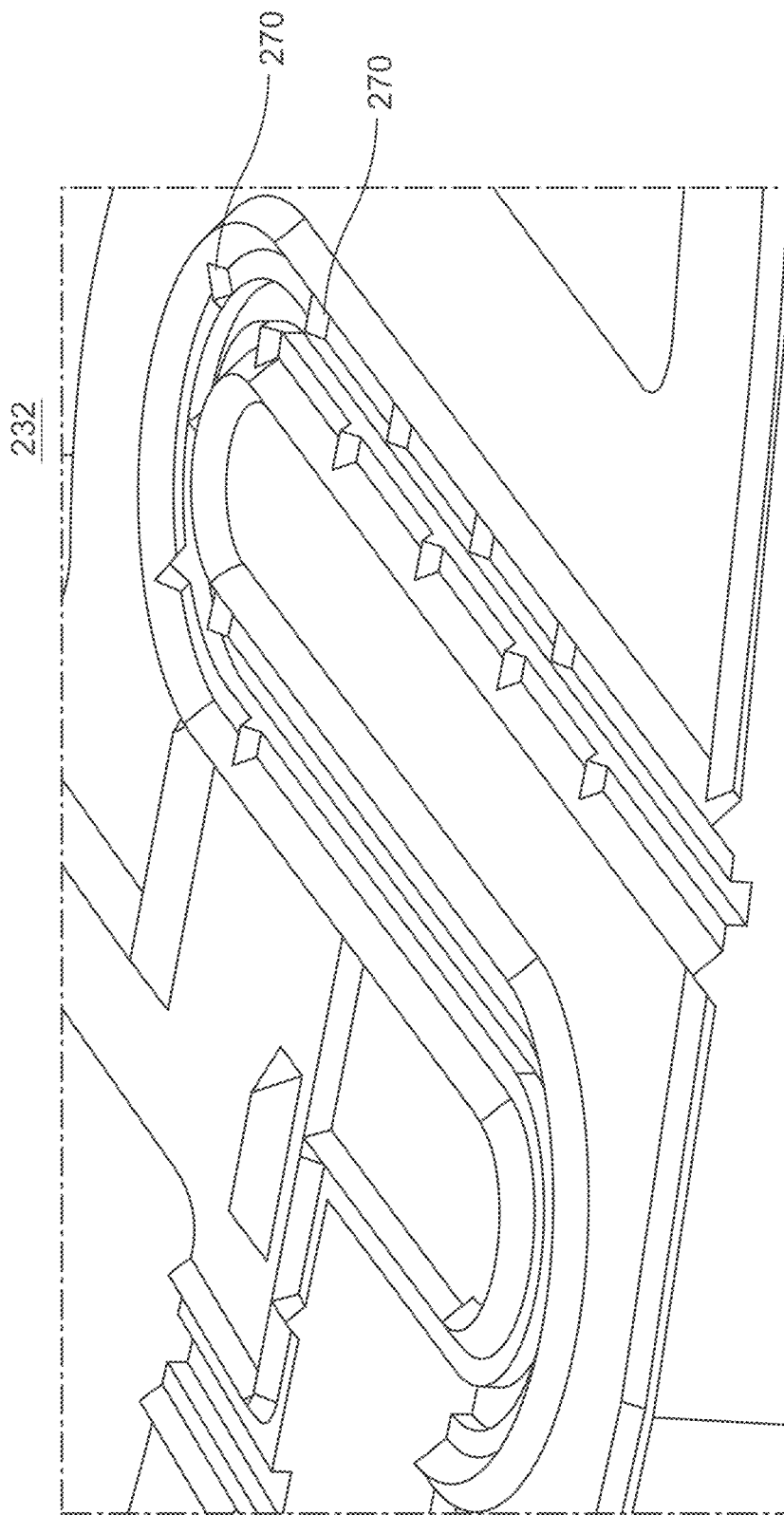
FIG. 4 illustrate a perspective view of design aspects of the conduits of FIGS. 2, 3A-3D.

FIGS. 3A-3D illustrate variations of the formation of the obstructive features 270 in the conduit 232 as described for FIG. 2, according to example embodiments. For example, FIG. 3D illustrates the formation of the obstructive features 270 in straight and curved parts of the conduit 232. FIG. 4 illustrates additional detail on design aspects of the obstructive features 270 formed in the conduit 232.

Figure 5A:
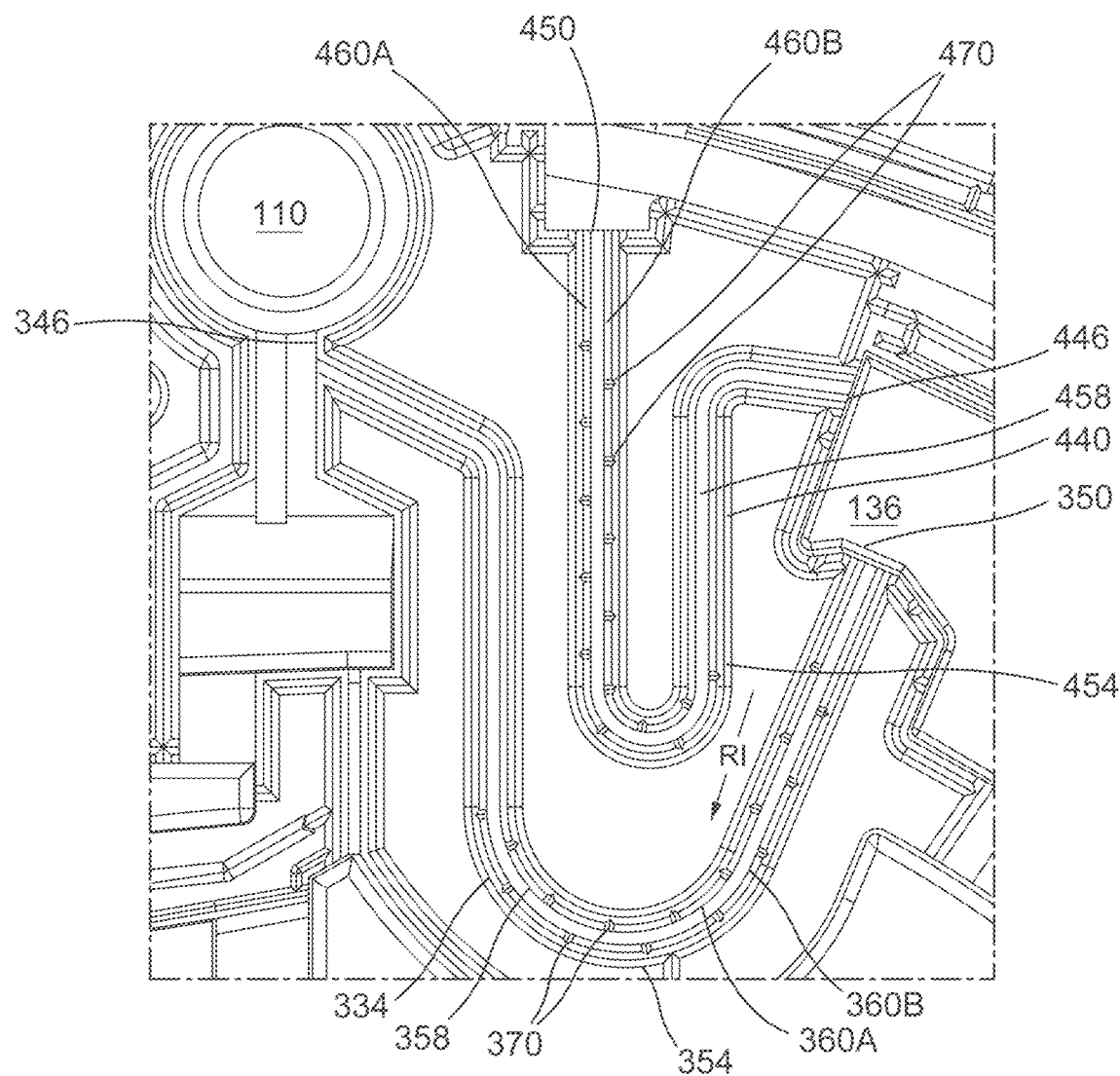
FIGS. 5A-5B are illustrations of additional conduits of a centrifugal rotor device, according to embodiments.
Figure 5B:
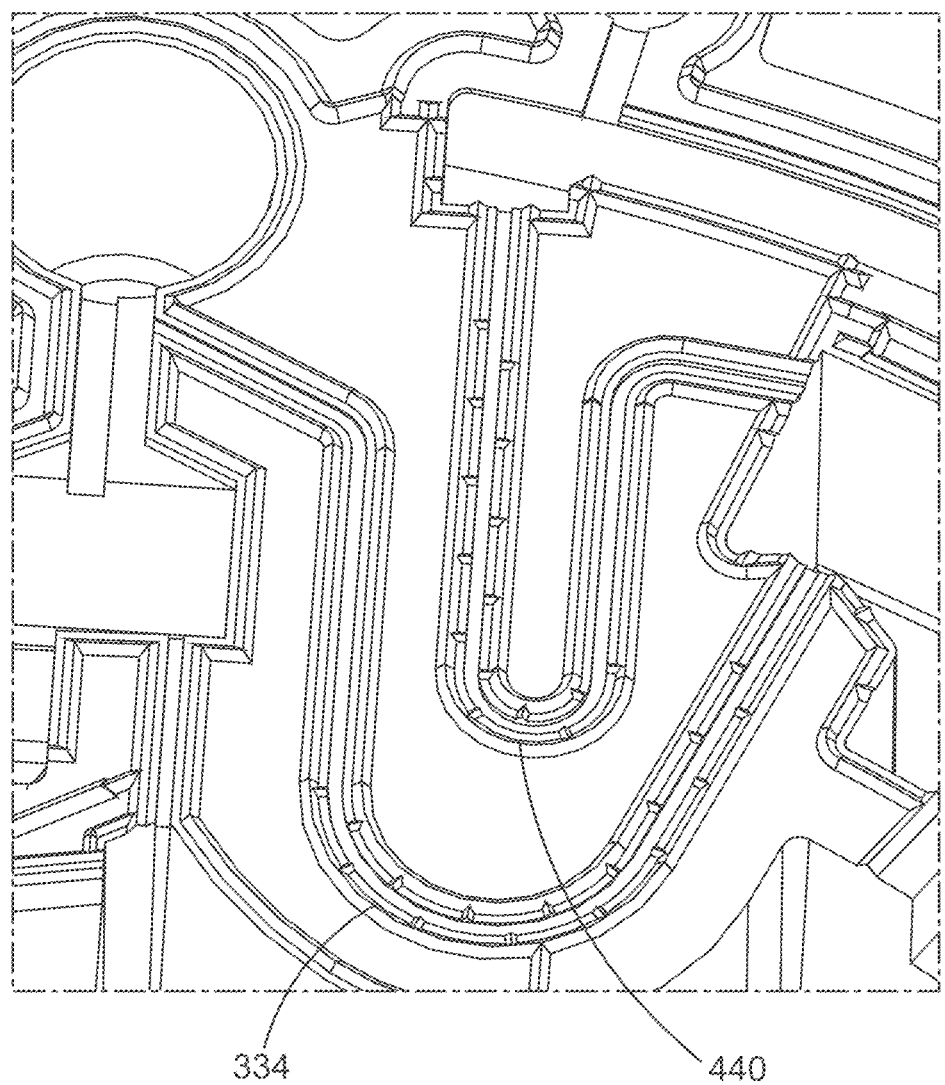

FIGS. 5A to 5B illustrate formation of obstructive features in the conduits 134, 140 (illustrated herein as reference characters 334, 440, respectively). It is understood that unless explicitly stated otherwise, the obstructive features in the conduits 334, 440 may be formed in a manner similar to as described for the conduit 232 above.

The conduit 334 can include an inlet portion 346 coupled to the chamber 110 (also sometimes referred to as a first chamber) and an outlet portion 350 coupled to the chamber 136 (also sometimes referred to as a second chamber). The conduit 334 includes a first/main channel 358, and second/ auxiliary channels 360A, 360B. The conduit 334 also includes one or more obstructive features 370 as illustrated.

Figure 6B:
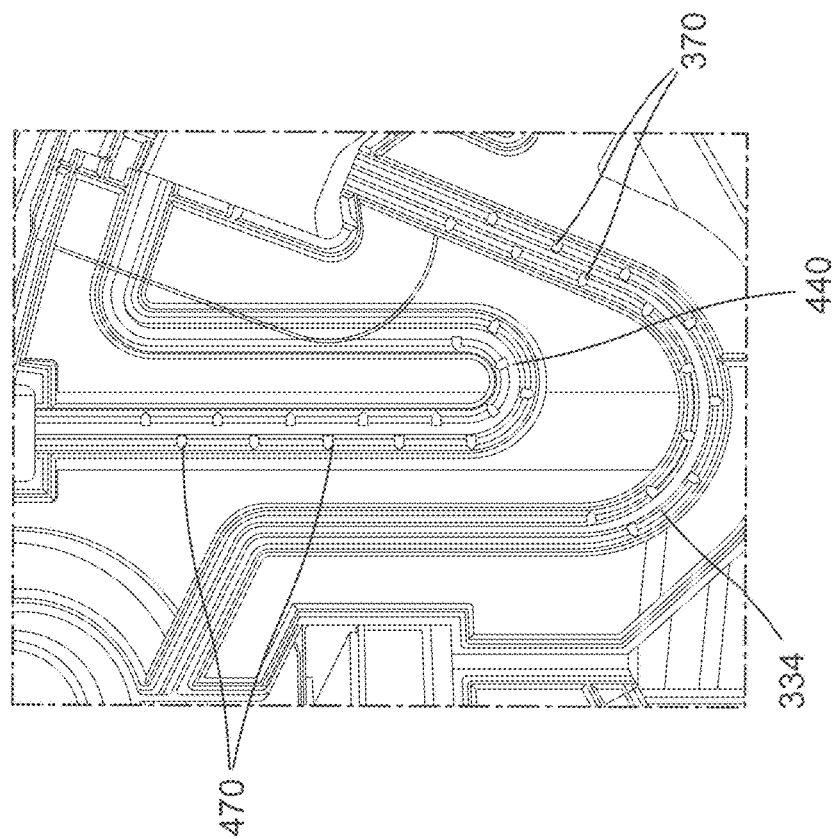
FIGS. 6A-6C illustrate variations in design of the conduits of FIG. 5A-5B, according to embodiments.
Figure 6A:
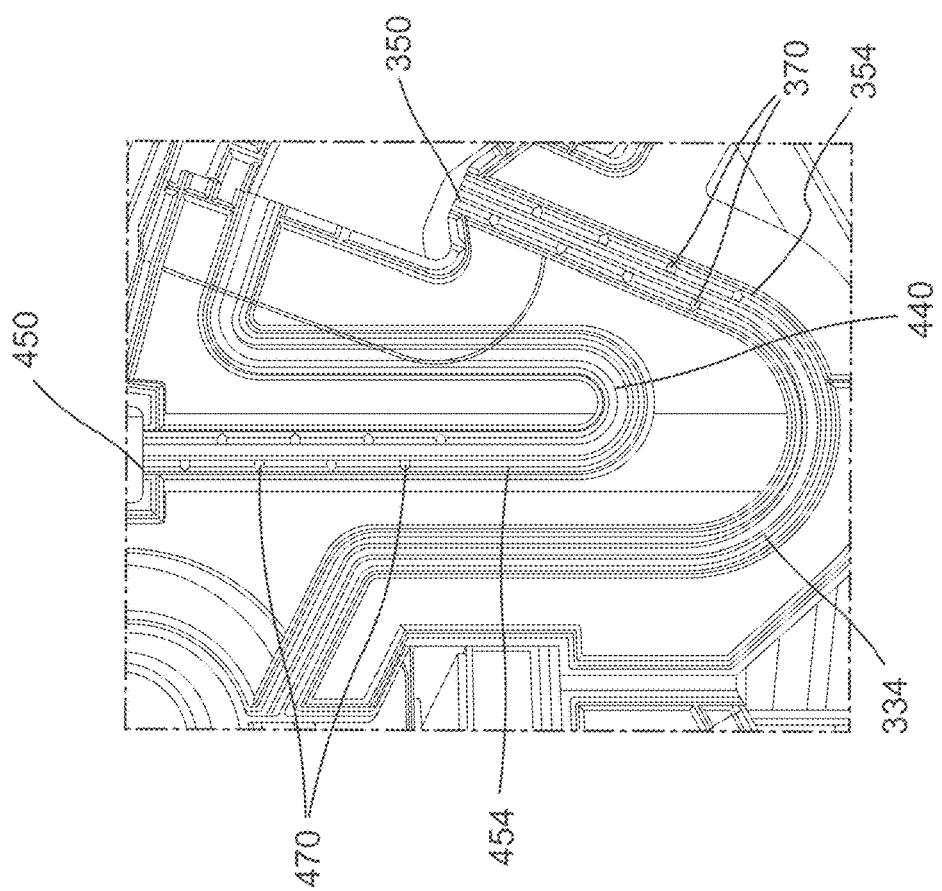
Figure 6C:
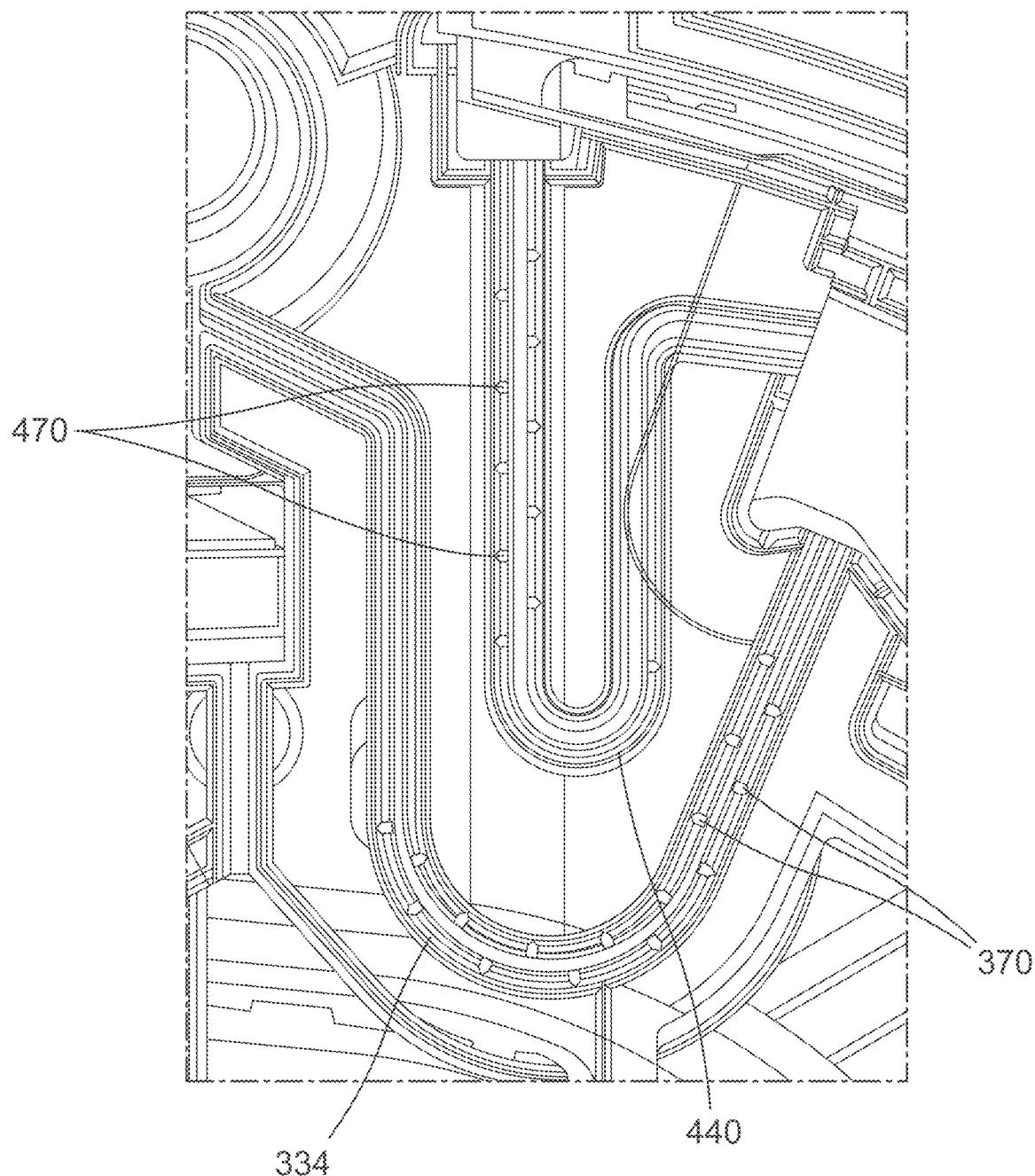

The conduit 440 can include an inlet portion 446 coupled to the chamber 136 (also sometimes referred to as a first chamber) and an outlet portion 450 coupled to the distribution channel 142 (also sometimes referred to as a second chamber). The conduit 440 includes a first/main channel 458, and second/auxiliary channels 460A, 460B. The conduit 434 also includes one or more obstructive features 470 as illustrated. FIGS. 6A-6C illustrate variations of the formation of the obstructive features 370, 470 in the conduits 334, 440 respectively.

In some embodiments, at least one of the conduits 232, 334, 440 can have one or more obstructive features formed therein. In some embodiments, each of the conduits 232, 334, 440 can have one or more obstructive features formed therein.

Generally referring to the conduits illustrated in FIGS. 2-6, in some embodiments, the one or more obstructive features (e.g., the features 270, 370, and/or 470) can include multiple obstructive features. In some embodiments, a first set of obstructive features is formed in a first auxiliary channel (e.g., the channel 260A) adjacent to the first channel (e.g., the channel 258), and a second set of obstructive features is formed in a second auxiliary channel (e.g., the channel 260B). In some embodiments, the conduit has a length associated therewith, and at least one obstructive feature of the first set of obstructive features is formed at the same point along the length of the conduit as at least one obstructive feature of the second set of obstructive features. In some embodiments, at least one obstructive feature of the first set of obstructive features is formed at a different point along the length of the conduit from at least one obstructive feature of the second set of obstructive features. In some embodiments, each obstructive feature of the first set of obstructive features and the second set of obstructive features is formed at a different point along the length of the conduit. In some embodiments, at least a portion of the one or more obstructive features extends into the first channel.

In some embodiments, the spacing between any two obstructive features is from about 0.2 mm, about 0.5 mm, about 1 mm, about 1.5 mm, about 2 mm, about 2.5 mm, about 3 mm, about 3.5 mm, about 4 mm, including all values and subranges in between. In some embodiments, the one or more obstructive features is selected from the group consisting of a protrusion, a weld (e.g., an energy director), and a hydrophobic region formed on a portion of a wall of the second channel. In some embodiments, the second channel is adjacent to a weld joint (e.g., an energy director). Said another way, the second channel can be adjacent the first channel on one side and adjacent a weld joint on the other side.

Still referring to FIGS. 2-6, in some embodiments, at least one of the first auxiliary channel (e.g., the channel 360A) and the second auxiliary channel (e.g., the channel 360B) is a capillary channel configured to permit movement of the fluid from the first chamber to the second chamber substantially due to capillary action. In some embodiments, both the first auxiliary channel (e.g., the channel 460A) and the second auxiliary channel (e.g., the channel 460B) are each a capillary channel configured to permit movement of the fluid from the first chamber to the second chamber substantially due to capillary action.

Referring to FIGS. 1-6, in some embodiments, the centrifugal rotor device includes a rim defining a radially inward direction and a radially outward direction, and the conduit can include an inlet portion, an outlet portion, and a curved portion formed between the inlet portion and the outlet portion. The curved portion is formed radially inward from the radially outermost of the inlet portion and the outlet portion, and the one or more obstructive features are formed at least in the curved portion of the conduit.

In some embodiments, the first chamber is a fluid dispensing chamber (e.g., the chamber 114, or the chamber 110) and the second chamber is a mixing chamber (e.g., the chamber 136). In some embodiments, the first chamber is a mixing chamber (e.g., the chamber 136) and the second chamber is a distribution channel (e.g., the ring/channel 142).

Figure 7A:
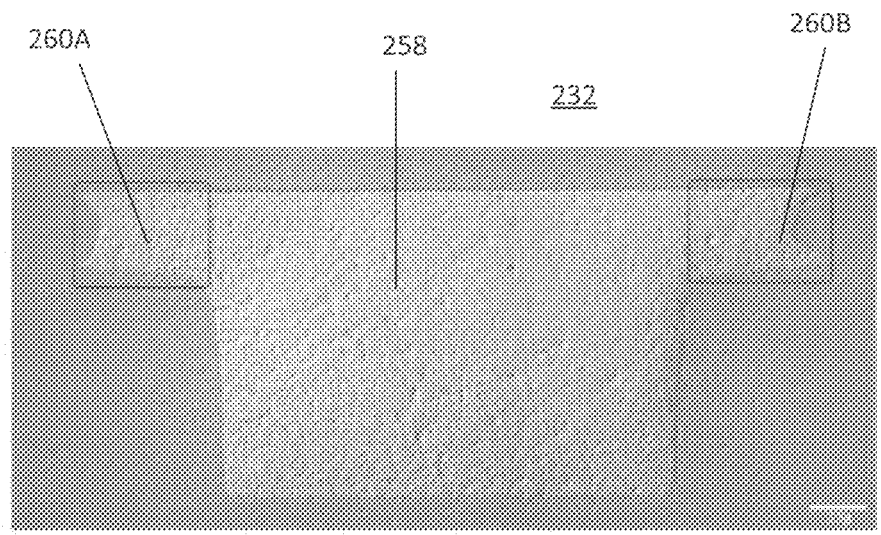
FIGS. 7A-7B, 8, 9A-9B, 10, and 11A-11C are images of cross-sections of conduits with (FIGS. 8, 9A-9B, 10, and 11A-11C) or without (FIGS. 7A-7B) obstructive features, according to embodiments.
Figure 7B:
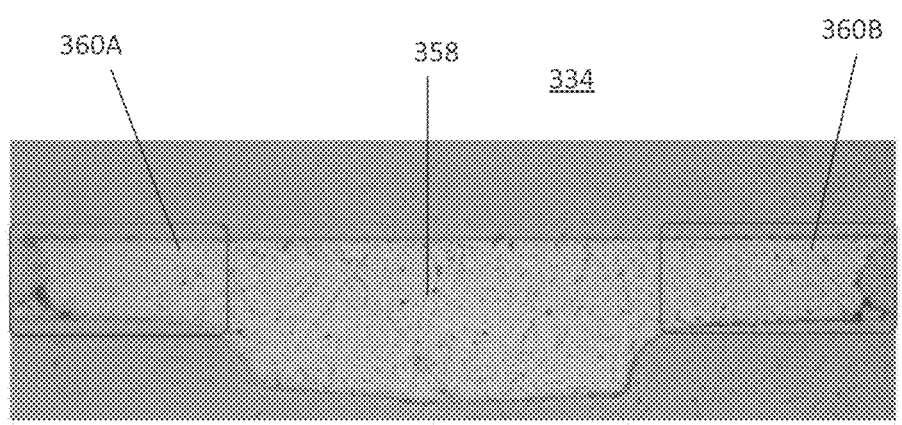
Figure 8:
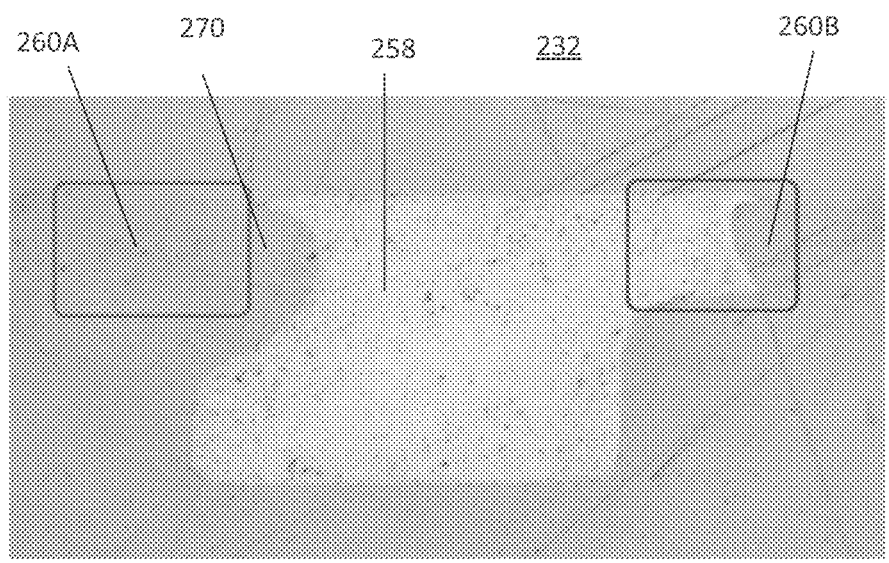

FIGS. 7A-7B are images of example cross sections of the conduit 232 (FIG. 7A) and the conduit 334 (FIG. 7B) at a point along the length where no obstructive features are present. The second channels 260A-260B, 360A-360B are prominently observed in both, as a product of ultrasonic welding. FIG. 8 is an image of a cross-section of the conduit 232 with the channel 260A completely occluded by an obstructive feature (here, a weld), a portion of which extends into the first channel 258.

Figure 9A:
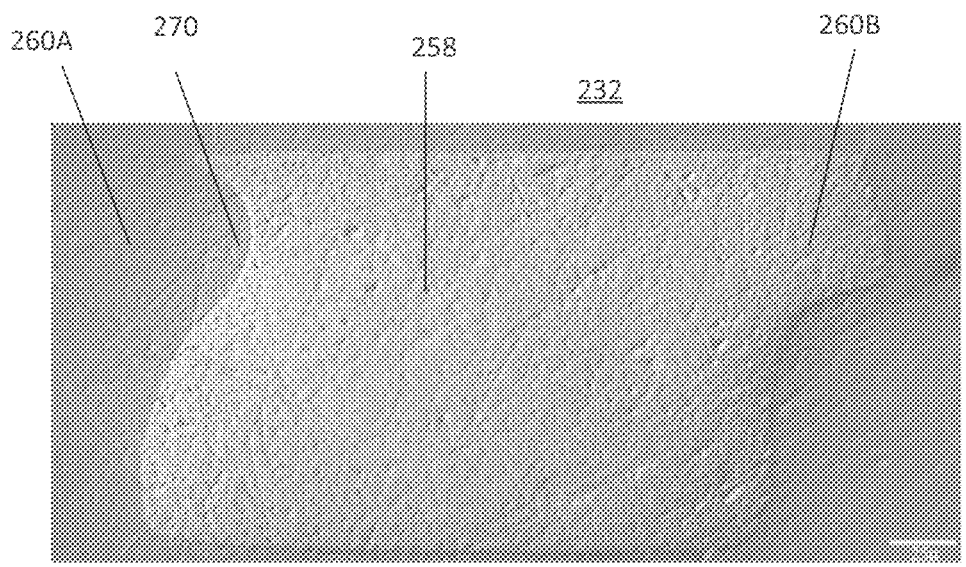
Figure 9B:
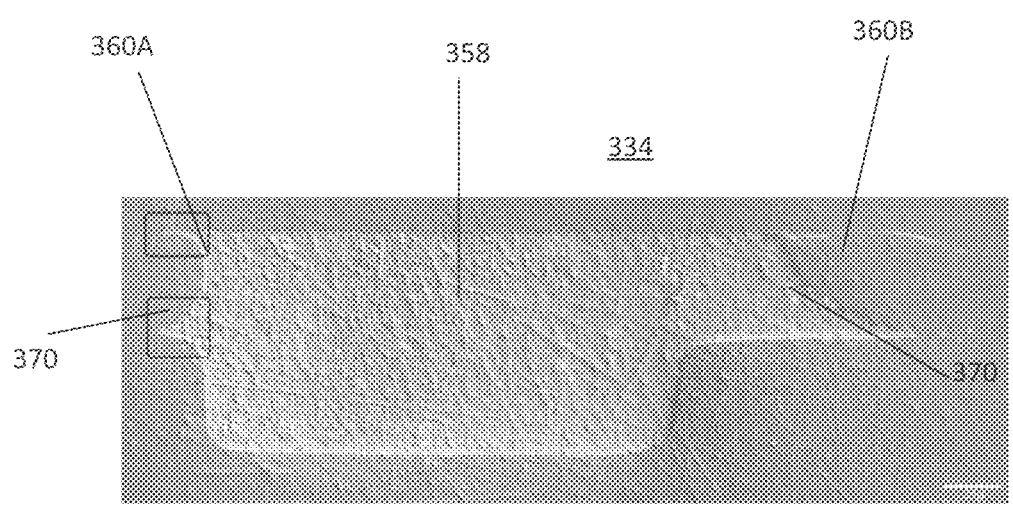
Figure 10:
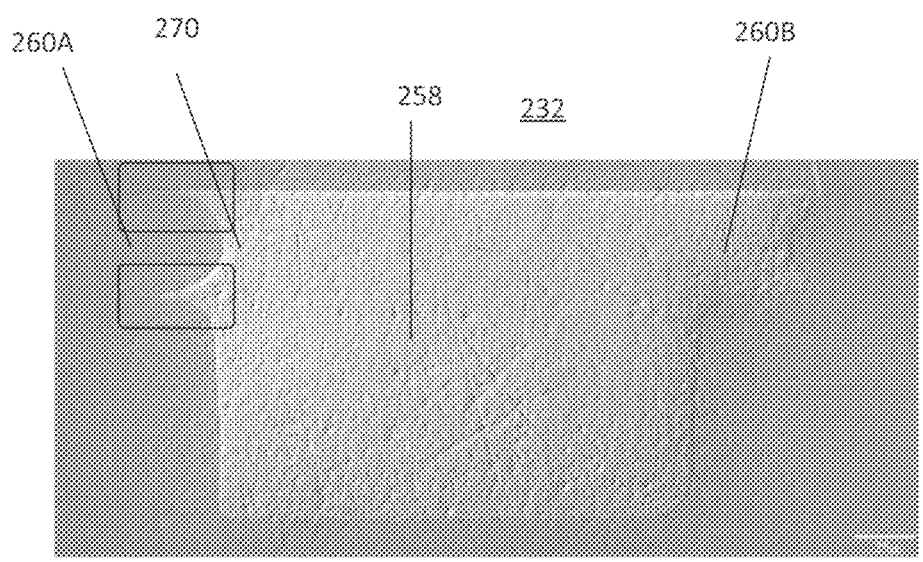

FIGS. 9A-9B are images of example cross sections of the conduit 232 (FIG. 9A) and the conduit 334 (FIG. 7B) with different sized obstructive features. FIG. 9A illustrates a relatively larger obstructive feature 270 that completely occludes the second channel 260A. FIG. 9B illustrates a relatively smaller obstructive feature 370 that partly occludes the second channel 360A. FIG. 10 is an image of an example cross section of the conduit 232 with a smaller obstructive feature than that of FIG. 9A.

Figure 11A:
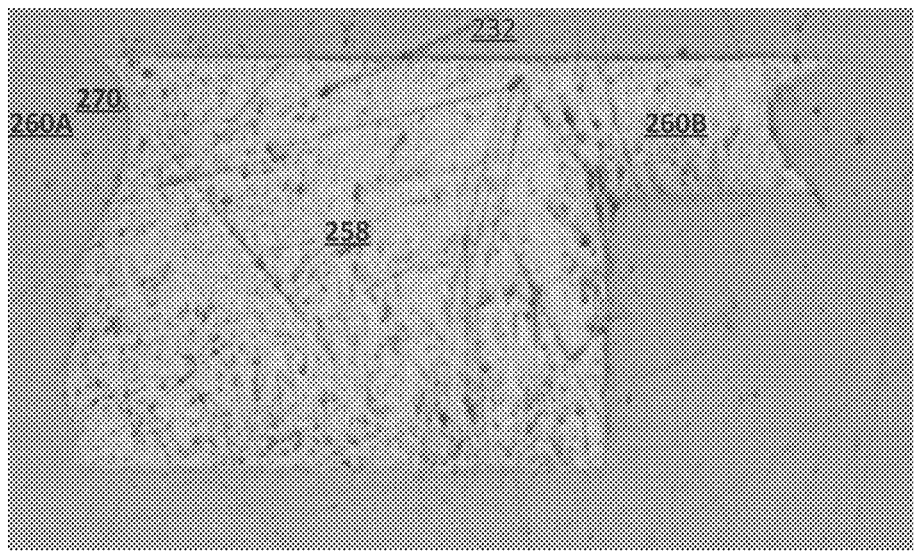
Figure 11B:
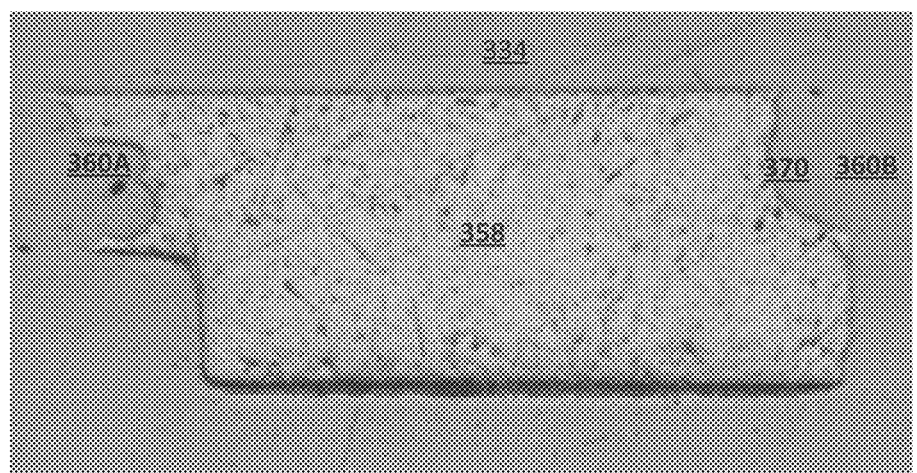
Figure 11C:
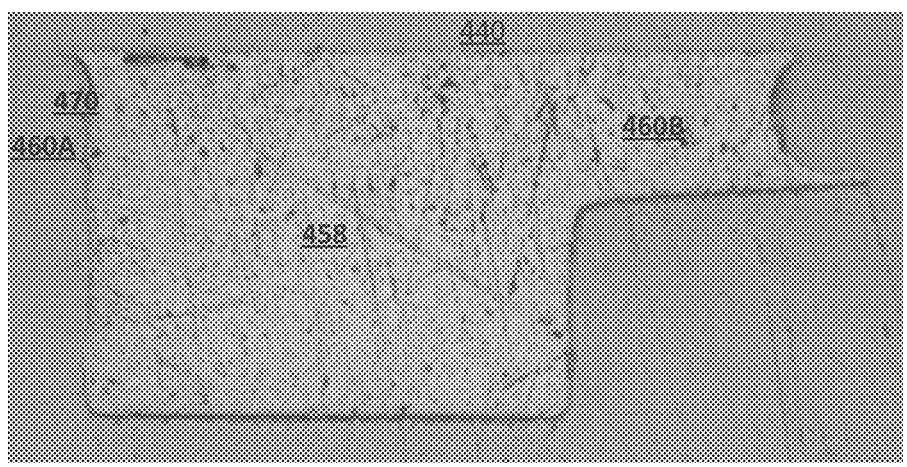
Figure 12A:
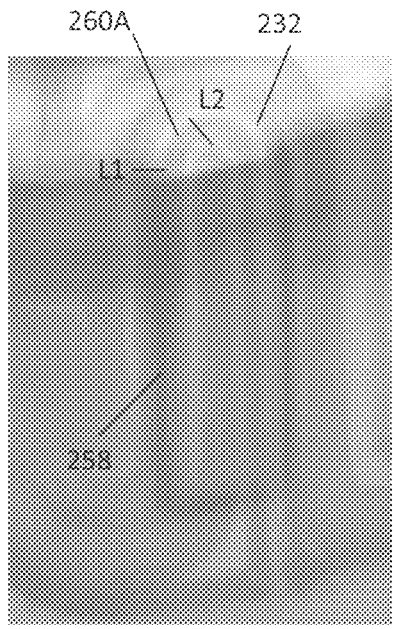
FIGS. 12A-12F are time-series images of fluid flow in a conduit without obstructive features, according to embodiments.
Figure 12B:
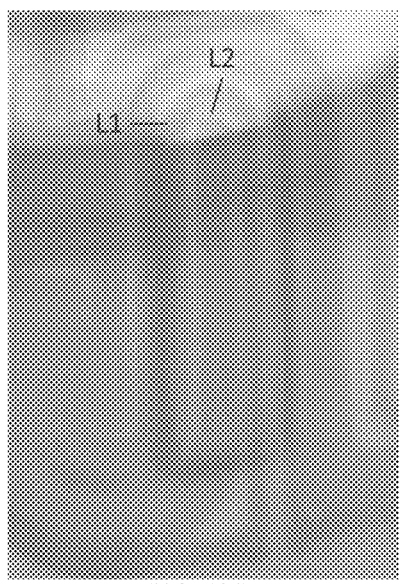
Figure 12C:
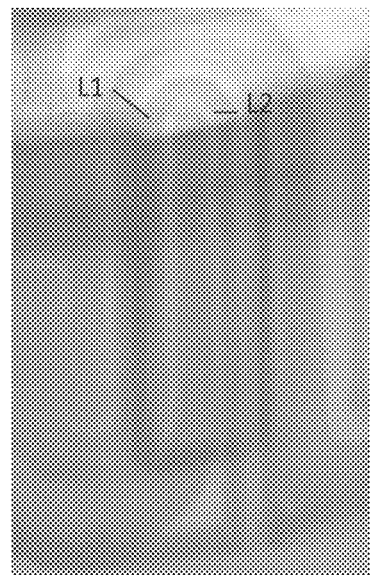
Figure 12D:
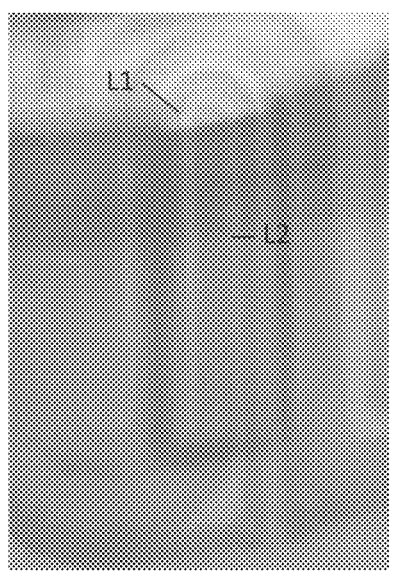
Figure 12E:
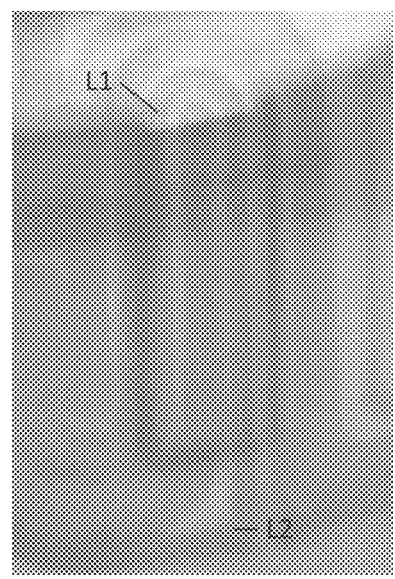
Figure 12F:
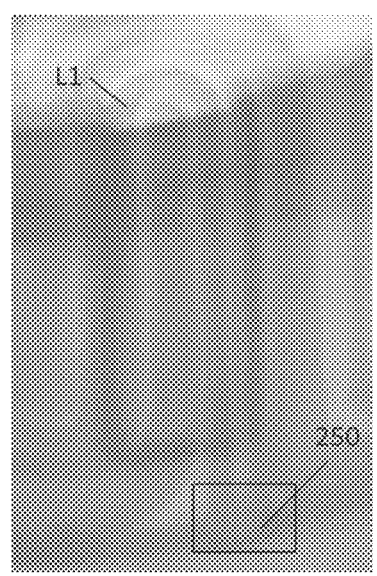
Figure 13A:
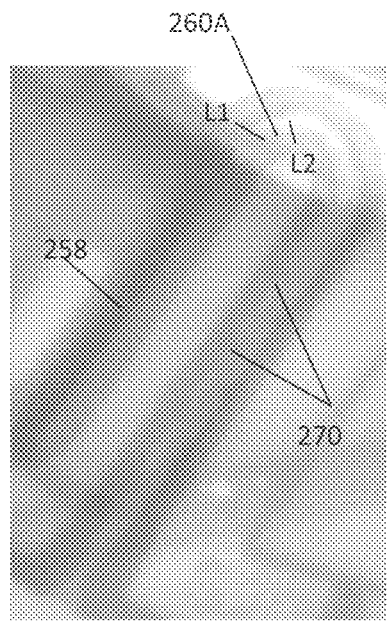
FIGS. 13A-13F are time-series images of fluid flow in a conduit with obstructive features, according to embodiments.
Figure 13B:
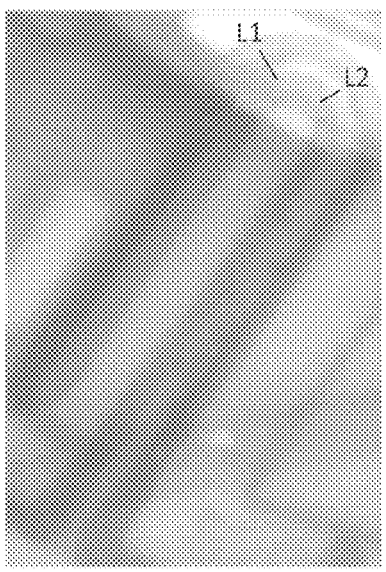
Figure 13C:
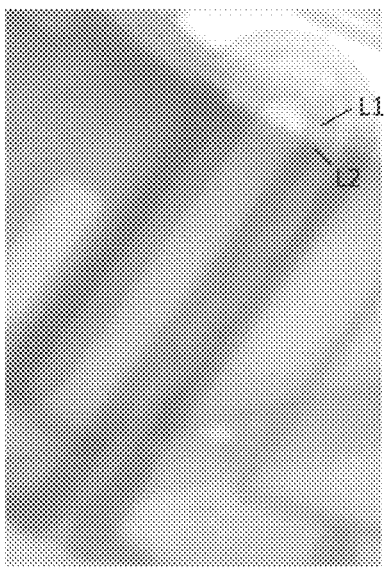
Figure 13D:
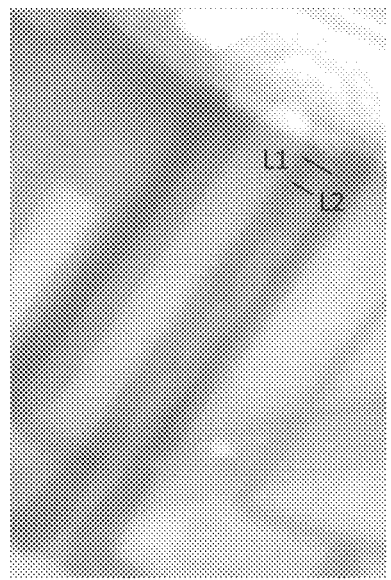
Figure 13E:
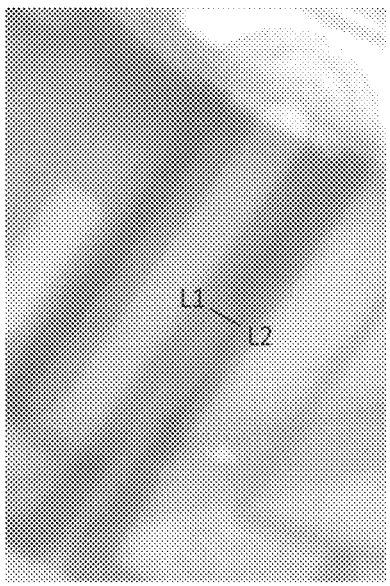
Figure 13F:
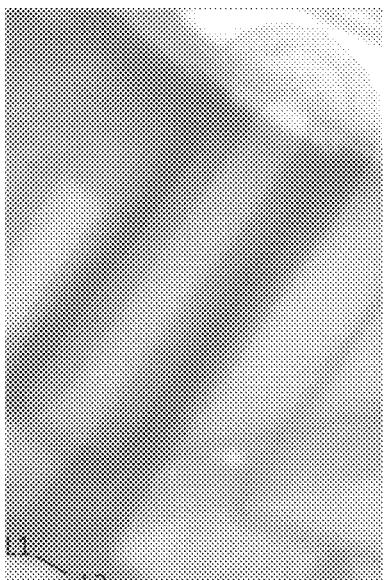

FIGS. 11A-11C illustrate cross sections of the conduits 232 (FIG. 11A), 334 (FIG. 11B) and 440 (FIG. 11C) for an example centrifugal rotor device. In each of FIGS. 11A-11C, at least one second channel is completely occluded.

Benefits of the use of obstructive features in conduits of centrifugal rotor devices as disclosed herein are illustrated in FIGS. 12A-12F, 13A-13F. FIGS. 12A-12F illustrate a time-lapse of fluid flow in the conduit 232 with no obstructive features present. The front profile of the fluid in the first channel 258 is illustrated by the reference character L1, and the front profile of the fluid in the second channel 260A is illustrated by the reference character L2. While little movement is seen in the movement of the fluid profile L1 in the first channel 258 between FIG. 12A-12C, the fluid profile L2 in the second channel 260A, due to capillary forces, reaches the outlet portion 250 (see FIGS. 12E, 12F) more quickly. At this point, the fluid from the second channel 260A is observed to spill into the first channel 258 and substantially occlude the first channel. This can lead to failure of the centrifugal rotor device and of downstream operations.

FIGS. 13A-13F illustrate a time-lapse of fluid flow in the conduit 232 with obstructive features 270 present. The front profile L1 lags L2 on occasion (see FIGS. 13B, 13C), but the presence of downstream obstructive features 270 permit L1 to substantially catch up to L2, such that both flow profiles in the first channel 258 and the second channel 260A reach the outlet portion at about the same time.

Some embodiments disclosed herein are directed to a centrifugal rotor device that includes a rim defining a radially inward direction and a radially outward direction. The device also includes a first chamber configured to receive a set of fluids and to substantially mix the set of fluids to generate a mixed fluid during use, the first chamber including a side wall. The device also includes a conduit including a coupling portion coupled to the side wall of the first chamber at a conduit inlet, the conduit being in fluid communication with the first chamber. In some embodiments, the coupling portion is formed between the radially inward direction and a direction perpendicular to the radially inward direction at an angle of from about 0 degrees to about 180 degrees from the radially inward direction. In some embodiments, the coupling portion is formed between the radially inward direction and the direction perpendicular to the radially inward direction at an angle of greater than 0 degrees from the radially inward direction. In some embodiments, the coupling portion is disposed at a distance of from about 0.025 mm to about 1 mm from a radially outward edge of the side wall.

In some embodiments, the angle is from about 70 degrees to about 80 degrees. In some embodiments, the conduit inlet is disposed at a distance of from about 0.5 mm to about 0.8 mm from the radially outward edge of the side wall.

In some embodiments, the first chamber is a mixing chamber and the centrifugal rotor device further includes a second chamber, the second chamber coupled to the conduit at a conduit outlet, the second chamber configured to receive the mixed fluid from the first chamber via the conduit.

In some embodiments, the set of fluids including a test fluid and a dilution fluid and the conduit is a first conduit. In such embodiments, the centrifugal rotor device can include a second chamber (e.g., the chamber 110) configured to hold the test fluid and a second conduit (e.g., the conduit 134 and/or the conduit 334) configured to fluidically couple the first chamber and the second chamber to transfer at least a portion of the test fluid from the second chamber to the first chamber. The centrifugal rotor device can also include a third chamber (e.g., the chamber 114) configured to hold the dilution fluid, and a third conduit (e.g., the conduit 132 and/or the conduit 232) configured to fluidly couple the first chamber and the third chamber to transfer at least a portion of the dilution fluid from the third chamber to the first chamber.

In some embodiments, at least one of the first conduit, second conduit, and third conduit include a first channel, a second channel formed adjacent to the first channel, the second channel in fluid communication with the first channel, the second channel having a dimension smaller than a smallest dimension of the main channel. The at least one of the first conduit, second conduit, and third conduit can further include one or more obstructive features present in the second channel, the one or more obstructive features configured to impede movement of fluid in the second channel.

In some embodiments, the conduit further includes an inlet portion, an outlet portion, and a curved portion formed between the inlet portion and the outlet portion. The curved portion is formed radially inward from the radially outermost of the inlet portion and the outlet portion.

Figure 14A:
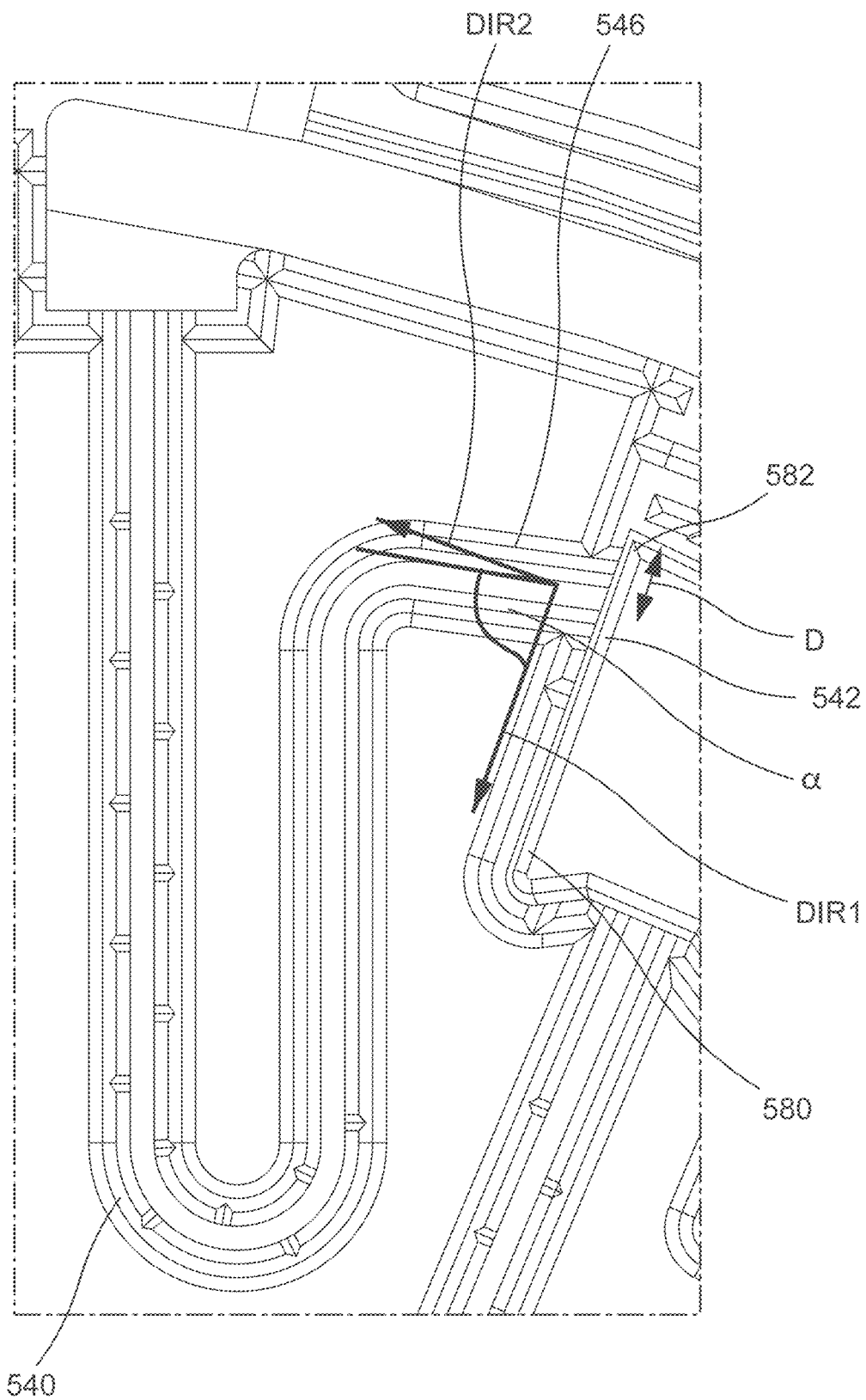
FIGS. 14A-14C are illustrations of design of coupling between a conduit inlet and a side wall of a chamber, according to embodiments.

FIG. 14A, illustrates the conduit 140 (referenced herein as reference character 540) having an coupling portion 546 coupled to a side wall 580 of the chamber 136 (see FIG. 1D) at a conduit inlet 542. In some embodiments, the coupling portion 546 can be similar to the inlet portion 446 as described herein. FIG. 14A also illustrates a radially inward direction DIR1, and a direction DIR2 that is perpendicular to DIR1. The coupling portion 546 is formed at an angle α relative to DIR1. In some embodiments, the angle α can take any suitable value including, but not limited to, about zero degrees, about 20 degrees, about 40 degrees, about 60 degrees, about 80 degrees, about 100 degrees, about 120 degrees, about 140 degrees, about 160 degrees, about 180 degrees, including all values and sub ranges in between. In some embodiments, the angle α can be between about 70 degrees and about 80 degrees.

As also illustrated in FIG. 14A, the coupling portion 546 is formed at a distance D from a radially outward edge 582 of the wall 580. In some embodiment, the distance D can take any suitable value including, but not limited to, 0.2 mm, 0.5 mm, 0.8 mm, 1 mm, 1.2 mm, 1.5 mm, including all values and sub ranges in between. It is understood that these values are not intended to be limiting, and can be scaled based on the dimensions of the conduit 540, and the centrifugal rotor device, and/or the like.

Figure 14B:
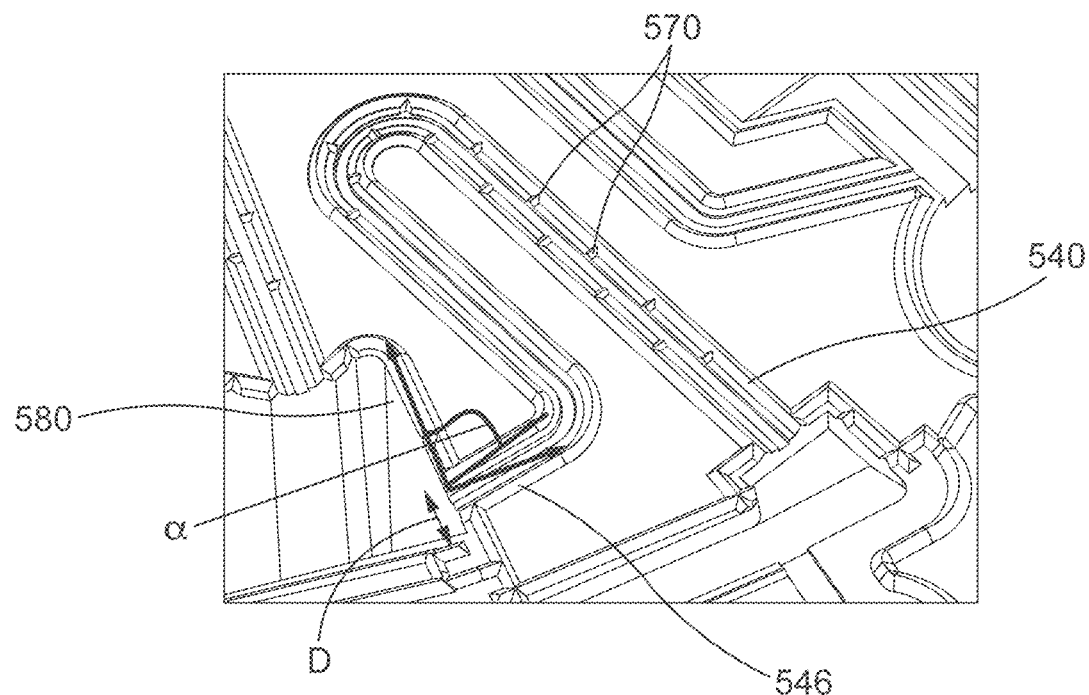
Figure 14C:
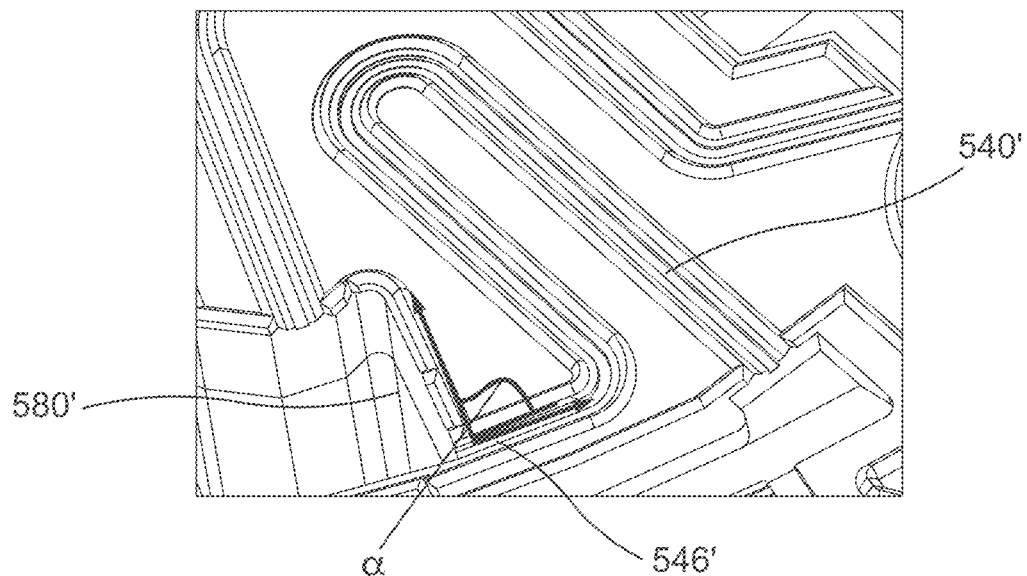

FIGS. 14B-14C are renderings of different positions of the coupling portion on the wall, according to example embodiments. For example, the angle α formed by the coupling portion 546 in FIG. 14B is relatively lesser than that formed by the coupling portion 546' in FIG. 14C, while the distance D is relatively smaller in FIG. 14C (almost negligible, not shown) than in FIG. 14B. FIG. 14B also illustrates obstructive structures 570 formed in the channel 540, while these are absent in the embodiment of the channel 540' illustrated in FIG. 14C.

Figure 15:
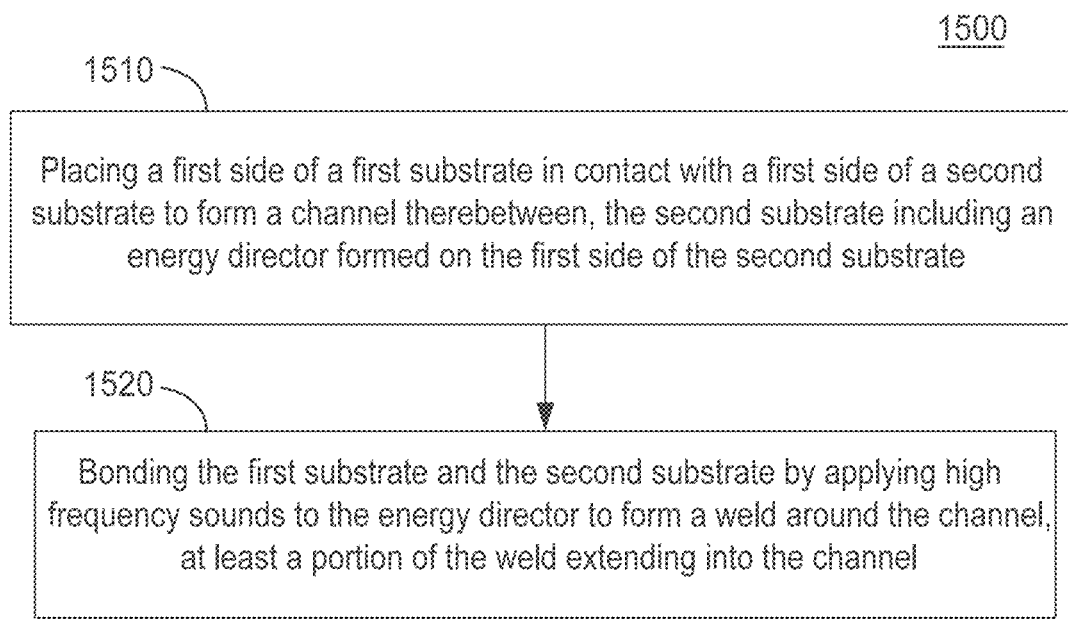
FIG. 15 is a method of fabricating a device, according to embodiments.

In this manner, during use of the chamber 136 as a mixing chamber as described herein, a volume of unmixed fluid that enters the conduit 540 is reduced by about 5%, about 10%, about 15%, about 20%, about 25%, about 30%, about 35%, about 40%, including all values and sub ranges in between. In some embodiments, when sedimentation accumulates near a radially outward section of the chamber 136 during use, modifying the distance D can reduce the amount of sediment that enters the conduit 540. Embodiments disclosed herein are hence beneficial for obtaining a more homogeneous, sediment-free sample for downstream analysis FIG. 15 illustrates a method 1500 of fabricating a device, according to some embodiments. For example, the method 1500 can be useful for fabricating any of the centrifugal rotor devices, and including some/all features, disclosed herein. The method 1500 includes, at step 1510, placing a first side of a first substrate in contact with a first side of a second substrate to form a channel therebetween (e.g., any of the conduits disclosed herein). The second substrate includes an energy director formed on the first side of the second substrate. The method 1500 also includes, at 1520, bonding the first substrate and the second substrate by applying high frequency sounds (e.g., via ultrasonic welding) to the energy director to form a weld around the channel, at least a portion of the weld extending into the channel (e.g., as an obstructive feature). In some embodiments, an edge of the energy director is formed at an angle of from about 20 degrees to about 160 degrees with respect to a longitudinal direction of the channel, including all values and sub ranges in between. In some embodiments, an edge of the energy director is formed at an angle of from about 45 degrees to about 135 degrees with respect to a longitudinal direction of the channel.

FIGS. 16A-16C are example illustrations of formation of an energy director adjacent to a channel, according to embodiments. FIGS. 16A-16C illustrate a first substrate 1610 (shown in dashed lines in FIG. 16A for convenience) and a second substrate 1620. The second substrate 1620 includes an energy director/weld joint 1630 and a channel 1640 formed thereon. In some embodiments, the substrates 1610, 1620 are bonded together using ultrasonic welding (e.g., as described in FIG. 15) to form any of the centrifugal rotor devices as disclosed herein. FIGS. 16A-16B illustrate a direction DIR3 generally corresponding to a direction along the longitudinal length of the channel 1640, and a direction DIR4 generally corresponding to a direction along the longitudinal length of the energy director 1630. In some embodiments, the direction DIR4 characterizes the direction of an edge of the energy director 1630 in the vicinity of, or substantially adjacent to, the channel 1640. In some embodiments, an angle β can generally characterize the angular separation between DIR3 and DIR4. The angle β can have any suitable value such as, about 30 degrees, about 40 degrees, about 60 degrees, about 80 degrees, about 100 degrees, about 120 degrees, about 140 degrees, about 160 degrees, including all values and ranges in between. In some embodiments, the angle β has a value ranging from about 45 degrees to about 135 degrees.

In this manner, when a second channel (e.g., any of the second channels 260A-260B, 360A-360B, 460A-460B) is formed during ultrasonic welding, a portion of the edge of the energy director 1630 can form a weld joint in at least a portion of the second channel as an obstructive structure and, in some embodiments, in the first channel 1640 as well. By controlling the angle β, the positioning and extent to which the obstructive structure protrudes into the second channel and (optionally) the first channel 1640 can be controlled.

FIG. 17 illustrates a method 1700 of fabricating a device, according to some embodiments. For example, the method 1700 can be useful for fabricating any of the centrifugal rotor devices, and including some/all features, disclosed herein. The method 1700 includes, at step 1710, placing a first side of a first substrate in contact with a first side of a second substrate to form a channel therebetween (e.g., any of the conduits disclosed). The second substrate includes an energy director formed on the first side of the second substrate and the channel includes a first channel (e.g., any of the first channels 258, 358, 458) and a second channel (e.g., any of the second channels 260A-260B, 360A-360B, 460A-460B) adjacent to the first channel, the second channel in fluid communication with the first channel. The second channel has a dimension smaller than a smallest dimension of the main channel. The energy director being relatively proximate to the second channel and relatively distal to the first channel.

The method 1700 also includes, at step 1720, bonding the first substrate and the second substrate by applying high frequency sounds to the energy director to form a weld. At least a portion of the weld extends into the second channel in the form of an obstructive feature (e.g., any of the obstructive features 270, 370, 470) configured to impede movement of fluid in the second channel during use.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The indefinite articles "a" and "an," as used herein, unless clearly indicated to the contrary, should be understood to mean "at least one." The terms "about," "approximately," and "substantially" as used herein in connection with a referenced numeric indication means the referenced numeric indication plus or minus up to 10% of that referenced numeric indication. For example, the language "about 50" units or "approximately 50" units means from 45 units to 55 units. Such variance can result from manufacturing tolerances or other practical considerations (such as, for example, tolerances associated with a measuring instrument, acceptable human error, or the like).

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

What is claimed is:

1. A centrifugal rotor device, comprising:
   a first chamber configured to hold a fluid;
   a second chamber configured to receive the fluid from the first chamber; and
   a conduit coupled to the first chamber at a conduit inlet and coupled to the second chamber at a conduit outlet, the conduit configured to permit movement of the fluid from the first chamber to the second chamber, the conduit including:
   a first channel;
   a second channel formed adjacent to the first channel, the second channel in fluid communication with the first channel, the second channel having a dimension smaller than the smallest dimension of the first channel; and
   one or more obstructive features present in the second channel, the one or more obstructive features configured to impede movement of the fluid in the second channel.

2. The centrifugal rotor device of claim 1, wherein the second channel is a first auxiliary channel formed adjacent a first side of the first channel, the one or more obstructive features formed in the first auxiliary channel including a first set of obstructive features formed in the first auxiliary channel,
   the conduit further including:
   a second auxiliary channel formed adjacent a second side of the first channel; and
   a second set of obstructive features formed in the second auxiliary channel.

3. The centrifugal rotor device of claim 2, the conduit having a length associated therewith, wherein at least one obstructive feature of the first set of obstructive features is formed at the same point along the length of the conduit as at least one obstructive feature of the second set of obstructive features.

4. The centrifugal rotor device of claim 2, the conduit having a length associated therewith, wherein at least one obstructive feature of the first set of obstructive features is formed at a different point along the length of the conduit from at least one obstructive feature of the second set of obstructive features.

5. The centrifugal rotor device of claim 2, the conduit having a length associated therewith, wherein each obstructive feature of the first set of obstructive features and the second set of obstructive features is formed at a different point along the length of the conduit.

6. The centrifugal rotor device of claim 2, wherein the first auxiliary channel and the second auxiliary channel are each a capillary channel configured to permit movement of the fluid from the first chamber to the second chamber substantially due to capillary action.

7. The centrifugal rotor device of claim 1, wherein the second channel is a capillary channel configured to movement of the fluid from the first chamber to the second chamber substantially due to capillary action.

8. The centrifugal rotor device of claim 1, wherein a portion of the one or more obstructive features extends into the first channel.

9. The centrifugal rotor device of claim 1, further comprising a rim defining a radially inward direction and a radially outward direction, the conduit including:
an inlet portion;
an outlet portion; and
a curved portion formed between the inlet portion and the outlet portion, the curved portion formed radially inward from the radially outermost of the inlet portion and the outlet portion,
the one or more obstructive features formed at least in the curved portion of the conduit.

10. The centrifugal rotor device of claim 1, the one or more obstructive features including a plurality of obstructive features, the spacing between any two obstructive features being from about 1 mm to about 2 mm.

11. The centrifugal rotor device of claim 1, the one or more obstructive features selected from the group consisting of: a protrusion, and a hydrophobic region formed on a portion of a wall of the second channel.

12. The centrifugal rotor device of claim 1, wherein the first chamber is a fluid dispensing chamber and the second chamber is a mixing chamber.

13. The centrifugal rotor device of claim 1, wherein the first chamber is a mixing chamber and the second chamber is a distribution channel.

14. The centrifugal rotor device of claim 1, wherein the second channel is adjacent a weld joint.

15. The centrifugal rotor device of claim 1, wherein the first chamber is a first fluid dispensing chamber configured to hold a first fluid, wherein the second chamber is a mixing chamber, wherein the conduit is a first conduit, and wherein the one or more obstructive features is a first set of obstructive features, further comprising:
a second fluid dispensing chamber configured to hold a second fluid;
a second conduit coupled to the second fluid dispensing chamber and coupled to the mixing chamber, the second conduit including a second set of obstructive features;
a distribution channel; and
a third conduit coupled to the mixing chamber and coupled to the distribution channel, the third conduit including a third set of obstructive features.

16. A centrifugal rotor device, comprising:
a rim defining a radially inward direction and a radially outward direction;
a first chamber configured to receive a set of fluids, the first chamber further configured to substantially mix the set of fluids to generate a mixed fluid during use, the first chamber including a side wall; and
a conduit including a coupling portion coupled to the side wall of the first chamber at a conduit inlet, the conduit being in fluid communication with the first chamber, the coupling portion formed between the radially inward direction and a direction perpendicular to the radially inward direction at an angle of from about 0 degrees to about 180 degrees from the radially inward direction, the coupling portion disposed at a distance of from about 0.0250 mm to about 1 mm from a radially outward edge of the side wall.

17. The centrifugal rotor device of claim 16, wherein the first chamber is a mixing chamber, further comprising a second chamber, the second chamber coupled to the conduit at a conduit outlet, the second chamber configured to receive the mixed fluid from the first chamber via the conduit.

18. The centrifugal rotor device of claim 16, the set of fluids including a test fluid and a dilution fluid, wherein the conduit is a first conduit, further comprising:
a second chamber configured to hold the test fluid;
a second conduit configured to fluidly couple the first chamber and the second chamber to transfer at least a portion of the test fluid from the second chamber to the first chamber;
a third chamber configured to hold the dilution fluid;
a third conduit configured to fluidly couple the first chamber and the third chamber to transfer at least a portion of the dilution fluid from the third chamber to the first chamber.

19. The centrifugal rotor device of claim 16, the conduit further including an inlet portion, an outlet portion, and a curved portion formed between the inlet portion and the outlet portion, the curved portion formed radially inward from the radially outermost of the inlet portion and the outlet portion.

20. A method of fabricating a device, comprising:
placing a first side of a first substrate in contact with a first side of a second substrate to form a channel therebetween, the second substrate including an energy director formed on the first side of the second substrate, the channel including a first channel and a second channel adjacent to the first channel, the second channel in fluid communication with the first channel, the second channel having a dimension smaller than a smallest dimension of the main channel, the energy director being relatively proximate to the second channel and relatively distal to the first channel; and
bonding the first substrate and the second substrate by applying high frequency sounds to the energy director to form a weld, at least a portion of the weld extending into the second channel in the form of an obstructive feature, the obstructive feature configured to impede movement of fluid in the second channel during use.

* * * * *